United States Patent
Krueger

(10) Patent No.: US 9,089,495 B2
(45) Date of Patent: *Jul. 28, 2015

(54) HAIR TREATMENT AGENT CONTAINING SELECTED FATTY ACID AMIDES AND SELECTED OIL BODIES

(71) Applicant: Henkel AG & Co. KGaA, Duesseldorf (DE)

(72) Inventor: Marcus Krueger, Ellerhoop (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/496,118

(22) Filed: Sep. 25, 2014

(65) Prior Publication Data

US 2015/0050228 A1  Feb. 19, 2015

Related U.S. Application Data

(63) Continuation of application No. PCT/EP2013/052931, filed on Feb. 14, 2013.

(30) Foreign Application Priority Data

Mar. 29, 2012 (DE) .......... 10 2012 205 089

(51) Int. Cl.
  *A61Q 5/12* (2006.01)
  *A61K 8/49* (2006.01)
  *A61K 8/92* (2006.01)
  *A61Q 5/00* (2006.01)
  *A61Q 17/04* (2006.01)
  *A61K 8/37* (2006.01)

(52) U.S. Cl.
  CPC .......... *A61K 8/4946* (2013.01); *A61K 8/37* (2013.01); *A61K 8/92* (2013.01); *A61K 8/922* (2013.01); *A61Q 5/00* (2013.01); *A61Q 5/004* (2013.01); *A61Q 5/12* (2013.01); *A61Q 17/04* (2013.01)

(58) Field of Classification Search
  CPC .......... A61Q 5/00; A61Q 5/12; A61K 8/37; A61K 8/92; A61K 8/922; A61K 8/4946
  USPC .......... 424/70.1, 70.12, 70.122, 70.2
  See application file for complete search history.

(56) References Cited

U.S. PATENT DOCUMENTS

| 4,873,294 | A * | 10/1989 | O'Lenick et al. .......... 525/419 |
| 7,964,694 | B2 | 6/2011 | Ferenz et al. |
| 2011/0142777 | A1 * | 6/2011 | Anzali et al. .......... 424/70.1 |

FOREIGN PATENT DOCUMENTS

| DE | 10201063590 A1 * | 9/2011 | .......... A61K 8/37 |
| DE | 102010063590 A1 | 9/2011 | |
| DE | 102010062640 A1 | 10/2011 | |
| DE | 102010062643 A1 | 10/2011 | |

OTHER PUBLICATIONS

PCT International Search Report (PCT/EP2013/052931) dated Jun. 19, 2013.
Anonymous, "Conditioning Agent for Fiber Alignment and Reduced Friction", Internet Citation, Oct. 31, 2011, XP007921795, Retrieved from the Internet on Apr. 17, 2013, URL: http://www.cosmeticsandtoiletries.com/formulating/function/moisturizer/132918958.html#.

* cited by examiner

*Primary Examiner* — Eisa Elhilo
(74) *Attorney, Agent, or Firm* — P. Scott Smith

(57) ABSTRACT

The present invention relates to hair treatment agents containing a synergistic combination of selected fatty acid amides and oil bodies selected from ester oils and vegetable oils.

20 Claims, No Drawings

HAIR TREATMENT AGENT CONTAINING SELECTED FATTY ACID AMIDES AND SELECTED OIL BODIES

FIELD OF THE INVENTION

The present invention generally relates to hair treatment agents comprising a synergistic combination of selected fatty acid amides and oily bodies, selected from the ester oils and the vegetal oils.

BACKGROUND OF THE INVENTION

There is a need to further improve hair care products and to provide them with additional advantageous properties. In particular, a care complex should be made available that ideally can also be used in combination with oxidizing agents and surfactant agents.

The environmental impact and oxidative hair treatments frequently lead to worsened combability of the dry and wet hair. Furthermore, the gloss and the moisture balance are adversely affected by the aggressed external structure of the keratinic fibers. Another consequence of repeated treatments of the keratinic fibers with surfactant and/or oxidizing agents is a strong regreasing of the keratinic fibers as well as a strong tendency for increased formation of dandruff.

Therefore, an object of the present invention is to reduce the side effects of the environmental impact and of oxidative as well as surfactant hair treatments preferably already during the oxidative or surfactant hair treatment, but also after the oxidative or surfactant hair treatment, without worsening the efficiency of the oxidative or surfactant cosmetic, in particular in regard to color intensity, color fastness, lightening power or waving, as well as preventing regreasing of the keratinic fibers and the increased formation of dandruff. Moreover, the oxidative treatment in the form of a 2-in-1 product for the keratin-containing fibers, especially human hair, should also be linked in one application step with the application of an effective protection of the fibers against environmental influences, for example a UV protection.

In principle, fatty acid amides are known chemical compounds and are also already used as ingredients in hair care agents. Silicones are likewise known in hair treatment agents. They are frequently employed to improve the properties of the hair. However, these known substances cannot achieve the objects in a satisfactory manner. In the following, when an active substance complex is mentioned, this term refers to the ingredients a) and b) that are mandatorily comprised in the hair treatment agents according to the invention.

Furthermore, other desirable features and characteristics of the present invention will become apparent from the subsequent description of the invention and the appended claims, taken in conjunction with the accompanying drawings and this background of the invention.

BRIEF SUMMARY OF THE INVENTION

A hair treatment agent, comprising—based on its weight— a) 0.01 to 15 wt % of a fatty acid amide according to the Formula (I)

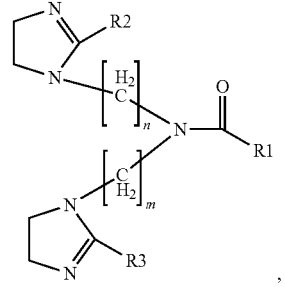

Formula (I)

in which R1, R2 and R3 independently of each other stand for a linear branched or unbranched C6 to C30, preferably C8 to C24, more preferably C12 to C22 and most preferably C12 to C18 alkyl or alkylene group, wherein furthermore R2 is preferably the same as R3 and most preferably R1 equals R2 equals R3, and n and m stand independently of one another for whole numbers from 1 to 10, preferably 2 to 6 and most preferably for 2, 3 and/or 4, wherein most preferably n=m; and b) at least one oily body, selected from the ester oils and/or the vegetal oils in a total amount of 0.01 to 95 wt % relative to the total composition.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The active substance complex according to the invention leads to an improved finish, an improved gloss, an improved moisture balance as well as protection against destructuration of the keratin-containing fibers, in particular human hair, by UV radiation and quite particularly for protection against oxidative damage, in particular for maintaining hair growth, for preventing hair loss and for preventing regreasing of the keratinic fibers as well as for increasing the wash resistance of dyed keratinic fibers. Consequently, a first subject matter of the present invention is a hair treatment agent comprising— based on its weight—
  a) 0.01 to 15 wt %, based on the total composition, of at least one fatty acid amide according to the Formula (I)

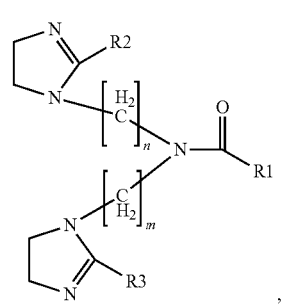

Formula (I)

in which R1, R2 and R3 independently of each other stand for a linear branched or unbranched C6 to C30, preferably C8 to C24, more preferably C12 to C22 and most preferably C12 to C18 alkyl or alkylene group, wherein furthermore R2 is preferably the same as R3 and most preferably R1 equals R2 equals R3, and n and m stand independently of one another for whole numbers from 1 to 10, preferably 2 to 6 and most preferably for 2, 3 and/or 4, wherein most preferably n=m, and b) at least one oily body, selected from the ester oils and/or the vegetal oils, in a total amount of 0.01 to 95 wt % relative to the total composition.

In a preferred embodiment of the present invention, the cosmetic agents serve for the treatment of keratinic fibers, especially human hair. Preferred agents according to the invention are therefore shampoos, hair dyes, conditioners or hair tonics for example.

The feel is defined by the tactility of a fiber bundle, wherein the person skilled in the art sensorially feels and assesses the parameters fullness and suppleness of the bundle.

Styling is understood to mean the capability to change the shape of a bundle of previously treated keratin-containing fibers, especially human hair. In hair cosmetics, one may also speak of hairstyling.

Maintaining the natural growth of keratinic fibers is understood to mean that the influences on natural hair growth by hair cosmetic treatments as described above, in particular by oxidative hair treatments, are offset and effects on the natural growth of the keratinic fibers in regard to thickness growth, longitudinal growth and/or in regard to hair loss are absent or at best minor.

According to the invention, an oxidative hair treatment is defined as the action on the hair of an oxidative cosmetic, comprising at least one oxidizing agent in a cosmetic carrier.

The hair treatment agent comprising the active substance complex according to the invention is preferably used immediately before, during or after the oxidative or surfactant treatment of the hair. In the context of the invention, the term "immediately before the oxidative or surfactant treatment of the hair" is understood to mean an application that is immediately followed by the oxidative or surfactant treatment of the hair, wherein the hair treatment agent comprising the active substance complex according to the invention was rinsed out of the hair beforehand or preferably was left on the hair and the hair is preferably still wet.

In the context of the invention, the term "after the oxidative or surfactant treatment of the hair" is understood to mean an application that either immediately follows the oxidative or surfactant treatment of the hair, wherein the hair treatment agent comprising the active substance complex according to the invention is applied onto the preferably still wet, towel dried hair after having rinsed out the oxidative or surfactant agent, or is first applied onto the dried or wet hair after a plurality of hours or days. In both cases the hair treatment agent according to the invention can be rinsed out again after a contact time of a few seconds up to 45 minutes or completely remain on the hair.

The action of the hair treatment agent according to the invention actually develops during the oxidative or surfactant treatment of the hair and also surprisingly continues after the hair treatment agent according to the invention has been intensively washed out.

The active substance complex according to the invention is preferably used in a cosmetic carrier. In particular, the cosmetic carriers can be aqueous or aqueous-alcoholic. An aqueous cosmetic carrier comprises at least 50 wt % water. In the context of the present invention, aqueous alcoholic cosmetic carriers are understood to mean aqueous solutions comprising 3 to 70 wt % of a $C_1$-$C_6$ alcohol, in particular, methanol, ethanol or propanol, isopropanol, butanol, isobutanol, tert-butanol, n-pentanol, isopentanols, n-hexanol, isohexanols, glycol, glycerin, 1,2-pentane diol, 1,5-pentane diol, 1,2-hexane diol or 1,6-hexane diol. The agents according to the invention can additionally comprise further organic solvents, such as, for example, methoxybutanol, benzyl alcohol, ethyl diglycol or 1,2-propylene glycol. Preference here is given to all water-soluble organic solvents. The component a) of the active substance complex according to the invention is a fatty acid amide of the general Formula (I).

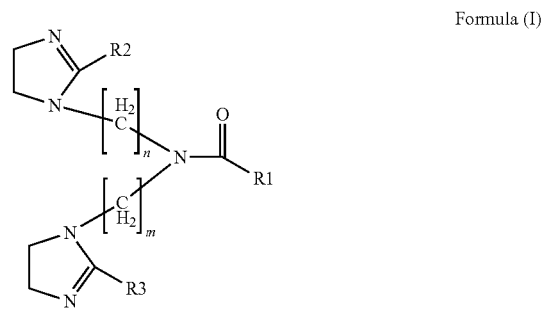

Formula (I)

in which R1, R2 and R3 independently of each other stand for a linear branched or unbranched C6 to C30, preferably C8 to C24, more preferably C12 to C22 and most preferably C12 to C18 alkyl or alkylene group. R1 to R3 preferably stand for capryl, caprylyl, octyl, nonyl, decanyl, lauryl, myristyl, cetyl, stearyl, oleyl, isostearyl, oleyl, behenyl or arachidyl. Furthermore, R2 is particularly preferably the same as R3 and most preferably R1 equals R2 equals R3. The letters n and m stand independently of one another for whole numbers from 1 to 10, preferably 2 to 6 and most preferably for 2, 3 and/or 4, wherein most preferably n=m. Most highly preferably, R1 equals R2 equals R3 and are selected from capryl, caprylyl, octyl, nonyl, decanyl, lauryl, myristyl, cetyl, stearyl, oleyl, isostearyl, oleyl, behenyl or arachidyl and n=m=2. Most preferably, R1=R2=R3 and are selected from lauryl, myristyl, cetyl, stearyl, isostearyl, oleyl, behenyl or arachidyl, among which cetyl, stearyl, isostearyl, oleyl or behenyl are particularly preferred and n=m=2 The most preferred compound of the Formula (I) is that which carries the INCI name Bis-Ethyl (isostearylimidazoline) Isostearamide. The latter compound is commercially available from Croda under the trade name Keradyn® HH.

The hair treatment agents according to the invention comprise the fatty acid amides according to the invention preferably in an amount of 0.01 to 15 wt %, particularly preferably 0.1 to 10 wt %, quite particularly preferably 0.1 to 7.5 wt %, most highly preferably 0.3 to 5.0 wt %, each relative to the weight of the ready for use hair treatment agent.

A second essential ingredient b) in the hair treatment agents is at least one ester oil and/or a vegetal oil.

The ester oils are defined as follows: ester oils are understood to mean the esters of $C_6$-$C_{30}$ fatty acids with $C_2$-$C_{30}$ fatty alcohols. The monoesters of fatty acids with alcohols containing 2 to 24 carbon atoms are preferred. Examples of the fatty acid moieties employed in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures. Examples of the fatty alcohol moieties in the ester oils are isopropyl alcohol, capronyl alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol as well as their industrial mixtures. According to the invention, isopropyl myristate (Rilanit® IPM), isononanoic acid C16-18 alkyl ester (Cetiol® SN), 2-ethylhexyl palmitate (Cegesoft® 24), stearic acid 2-ethylhexyl ester (Cetiol® 868), cetyl oleate, glycerin tricaprylate, cocofatty alcohol caprinate/-caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are particularly preferred.

The ester oils can of course also be alkoxylated with ethylene oxide, propylene oxide or mixtures of ethylene oxide and propylene oxide. In this regard, the alkoxylation can be on the fatty alcohol moiety as well as on the fatty acid moiety as well as on both parts of the ester oils. However, it is inventively preferred if the fatty alcohol was first alkoxylated and then esterified with fatty acid. These compounds are generally illustrated in the Formula (D4-II).

(D4-II)

R1 stands here for a saturated or unsaturated, branched or unbranched, cyclic saturated cyclic unsaturated acyl residue containing 6 to 30 carbon atoms, AO stands for ethylene oxide, propylene oxide or butylene oxide, X stands for a number between 1 and 200, preferably 1 and 100, particularly preferably between 1 and 50, quite particularly preferably between 1 and 20, highly preferably between 1 and 10 and most preferably between 1 and 5, R2 stands here for a saturated or unsaturated, branched or unbranched, cyclic saturated cyclic unsaturated alkyl, alkenyl, alkynyl, phenyl or benzyl residue containing 6 to 30 carbon atoms. Examples of the fatty acid moieties employed as the R1 residue in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures. Examples of the fatty alcohol moieties as the R2 residue in the ester oils are benzyl alcohol, isopropyl alcohol, capronyl alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol as well as their industrial mixtures. An inventively particularly preferred ester oil is available for example under the INCI name PPG-3 Benzyl Ether Myristate.

Additionally understood as ester oils are:

dicarboxylic acid esters such as di-n-butyl adipate, di-(2-ethylhexyl)adipate, di-(2-ethylhexyl)succinate and di-isotridecyl acetate as well as diol esters such as ethylene glycol dioleate, ethylene glycol di-isotridecanoate, propylene glycol di(2-ethylhexanoate), propylene glycol di-isostearate, propylene glycol di-pelargonate, butane diol di-isostearate, neopentyl glycol dicaprylate, as well as symmetrical, unsymmetrical or cyclic esters of carbon dioxide with fatty alcohols, e.g. glycerin carbonate or dicaprylyl carbonate (Cetiol® CC), trifatty acid esters of saturated and/or unsaturated linear and/or branched fatty acids with glycerin, fatty acid partial glycerides, under which are understood monoglycerides, diglycerides and their industrial mixtures. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures. Oleic acid monoglycerides are preferably employed.

The ester oils are used in the agents according to the invention in a total amount of 0.01 to 20 wt %, preferably 0.01 to 10.0 wt %, particularly preferably 0.01 to 7.5 wt %, most highly preferably 0.1 to 5.0 wt %. Of course it is inventively possible to also use a plurality of ester oils at the same time.

Other oily bodies according to the invention are:

vegetal oils. Exemplary natural oils include amaranth seed oil, apricot stone oil, argan oil, avocado oil, babassu oil, cotton seed oil, borage seed oil, camelina oil, safflower oil, peanut oil, pomegranate stone oil, grapefruit seed oil, hemp oil, hazelnut oil, elderberry seed oil, blackcurrent seed oil, jojoba oil, cocoa butter, linseed oil, *macadamia* nut oil, maize seed oil, almond oil, marula oil, evening primrose oil, olive oil, orange oil, palm oil, peach kernel oil, rape seed oil, rice oil, Hippophae Rhamnoides oil, sea buckthorn seed oil, sesame oil, shea butter, soya oil, sunflower oil, grape seed oil, walnut oil, wheat germ oil or wild rose oil and the liquid fractions of cocoa oil. Other triglyceride oils are suitable, if also limited, such as the liquid fractions of beef tallow as well as synthetic triglyceride oils, although these are not of vegetal origin.

Di-n-alkyl ethers containing a total of 12 to 36 carbon atoms, particularly 12 to 24 carbon atoms such as, for example, di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether and di-tert-butyl ether, diisopentyl ether, di-3-ethyldecyl ether, tert-butyl n-octyl ether, isopentyl n-octyl ether and 2-methylpentyl n-octyl ether. The compounds available as the commercial products 1,3-di-(2-ethylhexyl)cyclohexane (Cetiol® S) and di-n-octyl ether (Cetiol® OE) can be preferred.

These vegetal oils as well as the di-n-alkyl ethers are used in the agents according to the invention in a total amount of 0.01 to 20 wt %, preferably 0.01 to 10.0 wt %, particularly preferably 0.01 to 7.5 wt %, most highly preferably 0.1 to 5.0 wt %. Of course it is also inventively possible to use a plurality of these oils at the same time. Furthermore, it is also inventively possible to use at least one of these oils together with at least one ester oil.

In a particularly preferred embodiment of the present invention, selected quaternary ammonium compounds are preferably additionally used with the essential ingredients already described previously.

Quaternary ammonium compounds are principally monomeric cationic or amphoteric ammonium compounds, monomeric amines, amino amides, polymeric cationic ammonium compounds as well as polymeric amphoteric ammonium compounds. From this plurality of possible quaternary ammonium compounds, the following groups have proven to be particularly suitable and are each employed as such in an amount of 0.1 to 15.0 wt %. This quantity is also not less nor exceeded if a mixture of different compounds of the quaternary ammonium compounds is used.

Cationic surfactants of the Formula (Tkat1-1) form the first group of cationic surfactants.

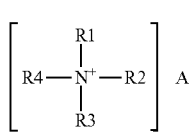

(Tkat1)

In the Formula (Tkat1), R1, R2, R3 and R4 each stand independently of each other for hydrogen, a methyl group, a phenyl group, a benzyl group, for a saturated, branched or unbranched alkyl residue with a chain length of 8 to 30 carbon atoms which can be optionally substituted with one or more hydroxy groups. A stands for a physiologically acceptable anion, for example halides such as chloride or bromide as well as methosulfates.

Exemplary compounds of the Formula (Tkat1) are lauryltrimethylammonium chloride, cetyltrimethylammonium chloride, cetyltrimethylammonium bromide, cetyltrimethylammonium methosulfate, dicetyldimethylammonium chloride, tricetylmethylammonium chloride, stearyltrimethylammonium chloride, distearyldimethylammonium chloride, lauryldimethylbenzylammonium chloride, behenyltrimethylammonium chloride, behenyltrimethylammonium bromide, behenyltrimethylammonium methosulfate.

Esterquats according to the Formula (Tkat2) form a preferred group.

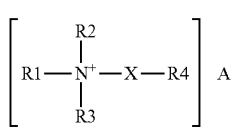

(Tkat2)

In which the R1, R2 and R3 residues are each independent of one another and may be the same or different. The R1, R2 and R3 residues mean:
- a branched or unbranched alkyl residue containing 1 to 4 carbon atoms which may comprise at least one hydroxy group, or
- a saturated or unsaturated, branched or unbranched or a cyclic saturated or unsaturated alkyl residue containing 6 to 30 carbon atoms which may comprise at least one hydroxy group, or
- an aryl or alkaryl residue, for example phenyl or benzyl, the residue (—X—R4), with the proviso that at most 2 of the R1, R2 or R3 residues may stand for this residue:
The residue (—X—R4) is comprised at least 1 to 3 times.

Herein X stands for:
1) —(CH2)n- with n=1 to 20, preferably n=1 to 10 and particularly preferably n=1-5, or
2) —(CH2-CHR5-O)n- with n=1 to 200, preferably n=1 to 100, particularly preferably 1 to 50, and particularly 1 to 20 with R5 meaning hydrogen, methyl or ethyl,
3) a hydroxyalkyl group containing one to four carbon atoms which can be branched or unbranched, and which comprises at least one and at most 3 hydroxy groups. Examples are: —CH$_2$OH, —CH$_2$CH$_2$OH, —CHOHCHOH, —CH$_2$CHOHCH$_3$, —CH(CH$_2$OH)$_2$, —COH(CH$_2$OH)$_2$, —CH$_2$CHOHCH$_2$OH, —CH$_2$CH$_2$CH$_2$OH and hydroxybutyl residues, and R4 stands for:
1) R6-O—CO—, in which R6 is a saturated or unsaturated, branched or unbranched or a cyclic saturated or unsaturated alkyl residue containing 6 to 30 carbon atoms which may comprise at least one hydroxy group, and which optionally may be further oxethylated with 1 to 100 ethylene oxide units and/or 1 to 100 propylene oxide units, or
2) R7-CO—, in which R7 is a saturated or unsaturated, branched or unbranched or a cyclic saturated or unsaturated alkyl residue containing 6 to 30 carbon atoms which may comprise at least one hydroxy group, and which optionally may be further oxethylated with 1 to 100 ethylene oxide units and/or 1 to 100 propylene oxide units, and A stands for a physiologically acceptable organic or inorganic anion and is defined here to also represent all A in the structures described hereinafter. The anion of all the described cationic compounds is selected from the halide ions, fluoride, chloride, bromide, iodide, sulfates of the general Formula RSO$_3^-$, in which R means saturated or unsaturated alkyl residues containing 1 to 4 carbon atoms, or anionic residues of organic acids such as maleate, fumarate, oxalate, tartrate, citrate, lactate or acetate.

Such products are marketed, for example, under the trade names Rewoquat®, Stepantex®, Dehyquart®, Armocare® and Akypoquat®. The products Armocare® VGH-70, Dehyquart® F-75, Dehyquart® C-4046, Dehyquart® L80, Dehyquart® F-30, Dehyquart® AU-35, Rewoquat® WE18, Rewoquat® WE38 DPG, Stepantex® VS 90 and Akypoquat® 131 are examples of these esterquats.

Further inventively particularly preferred compounds of the Formula (Tkat1-2) include the cationic betaine esters of the Formula (Tkat2.1).

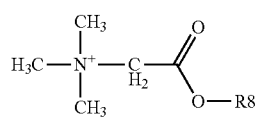

(Tkat2.1)

R8 corresponds to the meaning of R7.

The esterquats with the trade names Annocare VGH-70, as well as Dehyquart® F-75, Dehyquart® L80, Stepantex® VS 90 and Akypoquat® 131 are particularly preferred.

Cationic surfactants of the Formula (bI) are employed in narrow quantity ranges in preferred agents according to the invention, such that preferred hair treatment agents according to the invention are characterized in that they comprise 0.1 to 15 wt %, preferably 0.5 to 10 wt %, more preferably 1 to 10 wt %, still more preferably 1.5 to 10 wt % and in particular 2 to 5 wt % of at least one compound of the general Formula (I).

Formel (I)

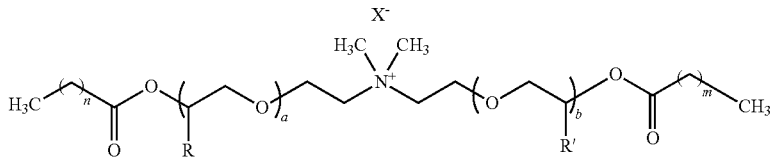

in which n and m independently of one another stand for whole numbers between 5 and 40, with the proviso that n+m≥38; particularly preferably n=m; most preferably n=m=20.

a and b independently of one another stand for whole numbers between 1 and 10; independently of one another particularly for 1, 2, 3, 4 or 5, where here the equation a+2≥b≥a−2 preferably applies and most preferably a=b=3.

R and R' independently of one another are selected from —H and —CH$_3$; preferably R=R', such that either PEG- or PPG-diesterquats are employed; quite particularly preferably R=R'=—CH$_3$ X— is a physiologically acceptable anion, a halide such as chloride, bromide or iodide, toluene sulfonate, methosulfate etc., and particularly preferably is methosulfate.

Especially when one of the compounds of the Formula (I) is used as described previously, it has been shown that the care effect of the agent according to the invention can be further augmented and in particular the stability of the agent can be further improved, if the agents comprise certain acylated diamines in addition to the compound(s) of the Formula (I).

Accordingly, preferred hair treatment agents according to the invention are characterized in that they additionally comprise 0.1 to 10 wt % of at least one compound of the Formula (II)

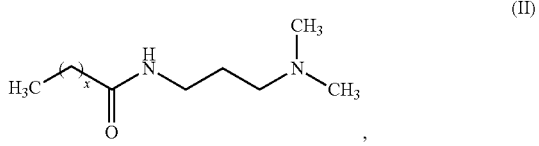

(II)

in which x stands for 18, 19, 20, 21, 22, 23 or 24.

Compounds of the Formula (II) with n=20 are particularly preferred in this regard. Most highly preferred agents according to the invention are characterized in that they always comprise a compound of the Formula (I) together with a compound of the general Formula (II).

Quaternary imidazoline compounds are another group. The structure of these compounds is shown below in the illustrated Formula (Tkat2).

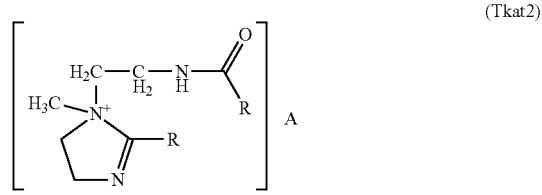

(Tkat2)

The R residues independently of each other each stand for a saturated or unsaturated, linear or branched hydrocarbon residue with a chain length of 8 to 30 carbon atoms. The preferred compounds of the Formula (Tkat2) each comprise the same hydrocarbon residue for R. The chain length of the R residue is preferably 12 to 21 carbon atoms. A stands for an anion as described above. Particular inventive examples are available for example under the INCI names Quaternium-27, Quaternium-72, Quaternium-83 and Quaternium-91. According to the invention, Quaternium-91 is most highly preferred.

In a particularly preferred embodiment of the invention, the agents according to the invention further comprise at least one amine and/or cationized amine, in particular an amido amine and/or a cationized amido amine with the following structural formula:

$$R1\text{-}NH\text{—}(CH_2)_n\text{—}N^+R^2R^3R^4 A \qquad (Tkat3)$$

in which R1 can be an acyl or alkyl residue containing 6 to 30 atoms which can be branched or unbranched, saturated or unsaturated, and wherein the acyl residue and/or the alkyl residue can comprise at least one OH group, and $R^2$, $R^3$ and $R^4$ independently of each other can be 1) hydrogen or 2) an alkyl residue containing 1 to 4 carbon atoms which can be the same or different, saturated or unsaturated, and 3) a branched or unbranched hydroxyalkyl group containing one to 4 carbon atoms with at least one and at most three hydroxy groups, for example —CH$_2$OH, —CH$_2$CH$_2$OH, —CHOHCHOH, —CH$_2$CHOHCH$_3$, —CH(CH$_2$OH)$_2$, —COH(CH$_2$OH)$_2$, —CH$_2$CHOHCH$_2$OH, —CH$_2$CH$_2$CH$_2$OH and hydroxybutyl residues, and A is an anion as described above and n means a whole number between 1 and 10.

A preferred composition is one, in which the amine and/or the quaternized amine according to the general Formula (Tkat3) is an amido amine and/or a quaternized amido amine, in which R1 means a branched or unbranched, saturated or unsaturated acyl residue containing 6 to 30 carbon atoms which can comprise at least one OH group. In this regard, a fatty acid residue from oils and waxes, in particular from naturally occurring oils and waxes, is preferred. Lanolin, beeswax or candellila waxes are examples of these.

Those amido amines and/or quaternized amido amines are also preferred in which R2, R3 and/or R4 in the Formula (Tkat3) mean a residue according to the general Formula CH$_2$CH$_2$OR5, in which R5 can mean alkyl residues containing 1 to 4 carbon atoms, hydroxyethyl or hydrogen. The preferred value of n in the general Formula (Tkat8) is a whole number between 2 and 5.

The alkylamido amines can both be present as such and be converted by protonation in appropriately acidic solution into a quaternary compound in the composition. The cationic alkylamido amines are inventively preferred.

Examples of such commercial products according to the invention are Witcamine® 100, Incromine® BB, Mackine® 401 and other Mackine® types, Adogen® S18V, and as the permanently cationic amido amines: Rewoquat® RTM 50, Empigen® CSC, Swanol® Lanoquat DES-50, Rewoquat® UTM 50, Schercoquat® BAS, Lexquat® AMG-BEO, or Incroquat® Behenyl HE.

The abovementioned cationic surfactants can be used individually or together in any combination, wherein amounts between 0.01 to 10 wt %, preferably in amounts of 0.01 to 7.5 wt % and quite particularly preferably in amounts of 0.1 to 5.0 wt % are comprised. In this regard, the best results of all are obtained with amounts of 0.1 to 3.0 wt %, each relative to the total composition of the relevant agent.

Other quaternary ammonium compounds are cationic and amphoteric polymers.

The cationic and/or amphoteric polymers can be homopolymers or copolymers or polymers based on naturally occurring polymers, wherein the quaternary nitrogen groups are comprised either in the polymer chain or preferably as a substituent on one or more of the monomers. The ammonium group-containing monomers can be copolymerized with non-cationic monomers. Suitable cationic monomers are unsaturated, radical polymerizable compounds that carry at least one cationic group, in particular ammonium substituted vinyl monomers, such as for example trialkylmethacryloxyalkylammonium, trialkylacryloxyalkylammonium, dialkyldiallylammonium and quaternary vinylammonium monomers containing cyclic, cationic nitrogen-containing groups, such as pyridinium, imidazolium or quaternary pyrrolidones, e.g. alkylvinylimidazolium, alkylvinylpyridinium, or alkylvinylpyrrolidone salts. The alkyl groups of these monomers are preferably lower alkyl groups, such as for example C1 to C7 alkyl groups, particularly preferably C1 to C3 alkyl groups.

The ammonium group-containing monomers can be copolymerized with non-cationic monomers. Exemplary suitable comonomers are acrylamide, methacrylamide, alkyl and dialkylacrylamide, alkyl and dialkylmethacrylamide, alkyl acrylate, alkyl methacrylate, vinyl caprolactone, vinyl caprolactam, vinyl pyrrolidone, vinyl esters, e.g. vinyl acetate, vinyl alcohol, propylene glycol or ethylene glycol, wherein the alkyl groups of these monomers are preferably C1 to C7 alkyl groups, particularly preferably C1 to C3 alkyl groups.

From the plurality of these polymers, particularly effective ingredients of the active substance complex according to the invention have proven to be: homopolymers of the general Formula —{CH$_2$—[CR$^1$COO—(CH$_2$)$_m$N$^+$R$^2$R$^3$R$^4$]}$_n$X$^-$, in which R$^1$=—H or —CH$_3$, R$^2$, R$^3$ and R$^4$ independently of each other are selected from C1-4 alkyl, -alkenyl or -hydroxyalkyl groups, m=1, 2, 3 or 4, n is a natural number and X$^-$ is a physiologically acceptable organic or inorganic anion. Regarding these polymers, those that are preferred in accordance with the invention meet at least one of the following conditions: R$^1$ stands for a methyl group, R$^2$, R$^3$ and R$^4$ stand for methyl groups, m has the value 2.

Exemplary physiologically acceptable counter ions X$^-$ include halide ions, sulfate ions, phosphate ions, methosulfate ions as well as organic ions such as lactate, citrate, tartrate and acetate ions. Methosulfate and halide ions are preferred, particularly chloride.

Suitable cationic polymers are for example copolymers according to the Formula (Copo) that are preferably comprised in the hair treatment agents according to the invention in an amount—based on their weight—of 0.001 to 5 wt %, preferably 0.0025 to 2.5 wt %, particularly preferably 0.005 to 1 wt %, more preferably 0.0075 to 0.75 wt % and in particular 0.01 to 0.5 wt %.

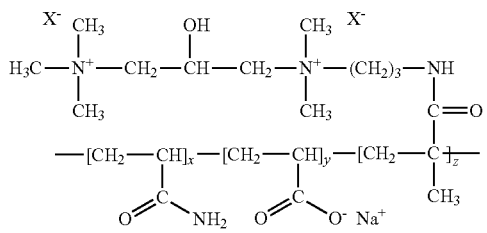

Formula (Copo)

in which:
x+y+z=Q
Q stands for values of 3 to 55 000, preferably 10 to 25 000, particularly preferably 50 to 15 000, more preferably 100 to 10 000, even more preferably 500 to 8000 and in particular 1000 to 5000,
x stands for (0 to 0.5) Q, preferably for (0 to 0.3) Q and in particular for the values 0, 1, 2, 3, 4, 5, wherein the value 0 is preferred,
y stands for (0.1 to 0.95) Q, preferably (0.5 to 0.7) Q and particularly for values of 1 to 24 000, preferably 5 to 15 000, particularly preferably 10 to 10 000 and in particular 100 to 4800,
z stands for (0.001 to 0.5) Q, preferably (0.1 to 0.5) Q and particularly for values of 1 to 12 500, preferably 2 to 8000, particularly preferably 3 to 4000 and in particular 5 to 2000.

A most highly preferred copolymer that has the structure as illustrated above is commercially available under the name polyquaternium-74.

A particularly suitable homopolymer is the optionally crosslinked poly(methacryloyloxyethyltrimethylammonium chloride) with the INCI name polyquaternium-37. Such products are commercially available for example under the trade names Rheocare® CTH (Cosmetic Rheologies) and Synthalen® CR (3V Sigma).

The homopolymer is preferably employed in the form of a non-aqueous polymer dispersion. Such polymer dispersions are commercially available under the trade names Salcare® SC 95 and Salcare® SC 96.

Suitable cationic polymers derived from naturally occurring polymers are cationic derivatives of polysaccharides, for example cationic derivatives of cellulose, starch or guar. Chitosan and chitosan derivatives are also suitable. Cationic polysaccharides have the general Formula G-O—B—N$^+$R$_a$R$_b$R$_c$A$^-$ G is an anhydroglucose residue, for example starch- or cellulose-anhydroglucose;
B is a divalent linking group, for example alkylene, oxyalkylene, polyoxyalkylene or hydroxyalkylene;
R$_a$, R$_b$ and R$_c$ independently of each other are alkyl, aryl, alkylaryl, arylalkyl, alkoxyalkyl or alkoxyaryl, each containing up to 18 carbon atoms, wherein the total number of the carbon atoms in R$_a$, R$_b$ and R$_c$ is preferably 20 at most;
A$^-$ is a typical counter anion and is preferably chloride.

Cationic, i.e. quaternized celluloses, are commercially available with different degrees of substitution, cationic charge density, nitrogen content and molecular weights. For example, polyquaternium-67 is commercially available under the trade names Polymer® SL or Polymer® SK (Amerchol). Another most highly preferred cellulose is commercially available from Croda under the trade name Mirustyle® CP. This is a Trimonium and Cocodimonium Hydroxyethylcellulose as a derivatized cellulose with the INCI name polyquaternium-72. Polyquaternium-72 can be used in solid form and also in pre-dissolved form in aqueous solution.

Additional cationic celluloses are Polymer JR® 400 (Amerchol, INCI name polyquaternium-10) and Polymer Quatrisoft® LM-200 (Amerchol, INCI name polyquaternium-24). Other commercial products are the compounds Celquat® H 100 and Celquat® L 200. Particularly preferred cationic celluloses are polyquaternium-24, polyquaternium-67 and polyquaternium-72.

Suitable cationic guar derivatives are marketed under the trade name Jaguar and have the INCI name Guar Hydroxypropyltrimonium Chloride. Other particularly suitable cationic guar derivatives are also commercially available from Hercules under the trade name N-Hance®. Other cationic guar derivatives are commercially available from Cognis under the trade name Cosmedia®. A preferred cationic guar derivative is the commercial product AquaCat® of Hercules. This raw material concerns an already pre-dissolved cationic guar derivative. The cationic guar derivatives are inventively preferred.

A suitable chitosan is available for example from Kyowa Oil & Fat, Japan, under the trade name Flonac®. A preferred chitosan salt is chitosonium pyrrolidone carboxylate, which is marketed for example under the name Kytamer® PC from Amerchol, USA. Other chitosan derivatives are freely available under the trade names Hydagen® CMF, Hydagen® HCMF and Chitolam® NB/101.

Another group of inventively outstanding polymers to be used are polymers based on glucose. A cationic alkyl oligoglucoside of this type is shown in the figure below.

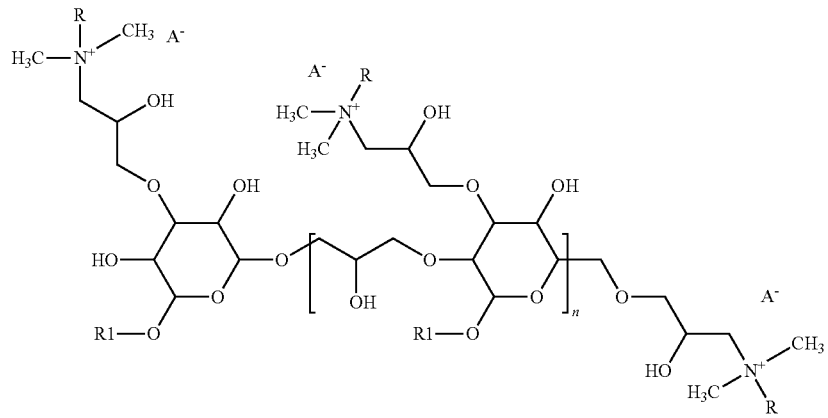

In the above depicted formula the R residues, independently of each other, stand for a linear or branched C6 to C30 alkyl residue, a linear or branched C6-C30 alkenyl residue, preferably the R residue stands for a residue R selected from: lauryl, myristyl, cetyl, stearyl, oleyl, behenyl or arachidyl.

The R1 residues, independently of each other, stand for a linear or branched C6-C30 alkyl residue, a linear or branched C6-C30 alkenyl residue, preferably the R residue stands for a residue selected from butyl, capryl, caprylyl, octyl, nonyl, decanyl, lauryl, myristyl, cetyl, stearyl, oleyl, behenyl or arachidyl. The R1 residues are particularly preferably the same. Even more preferably the R1 residues are selected from industrial mixtures of fatty alcohol fractions of C6/C8 fatty alcohols, C8/C10 fatty alcohols, C10/C12 fatty alcohols, C12/C14 fatty alcohols, C12/C18 fatty alcohols, and most preferably in this regard those industrial fatty alcohol fractions that are of vegetal origin. The counter ion to the cationic charge is a physiologically acceptable anion, for example halide, methosulfate, phosphate, citrate, tartrate, etc. The counter ion is preferably a halide, such as fluoride, chloride, bromide or methosulfate. The chloride anion is most preferred.

Particularly preferred examples of cationic alkyl oligoglucosides are the compounds with the INCI names polyquaternium-77, polyquaternium-78, polyquaternium-79, polyquaternium-80, polyquaternium-81 and polyquaternium-82. Most highly preferred cationic alkyl oligoglucosides have the trade names polyquaternium-77, polyquaternium-81 and polyquaternium-82.

Such compounds can be obtained under the name Poly Suga® Quat from Colonial Chemical Inc.

The cationic alkyl oligoglucosides are used in a total amount of 0.01 to 10.0 wt %, preferably 0.05 to 5.0 wt %, more preferably 0.1 to 3.0 wt % and most preferably in amounts of 0.2 to 2.0 wt %, each relative to the total weight of the composition. More mixtures of cationic alkyl oligoglucosides may, of course, also be inventively used. In this case it is preferred to use simultaneously a long chain and a short chain cationic alkyl oligoglucoside.

Another preferred cationic polymer can be obtained based on ethanolamine. The polymer is commercially available under the name polyquaternium-71.

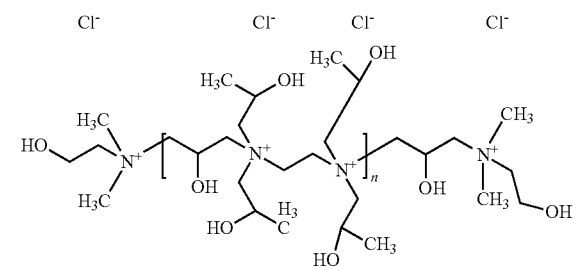

This polymer can be obtained for example under the name Cola® Moist 300P from Colonial Chemical Inc.

The polyquaternium-71 is used in a total amount of 0.01 to 10.0 wt %, preferably 0.05 to 5.0 wt %, more preferably 0.1 to 3.0 wt % and most preferably in amounts of 0.2 to 2.0 wt %, each relative to the total weight of the composition.

Furthermore, a cationic alkyl oligoglucoside, as shown in the following figure, can be particularly preferably used.

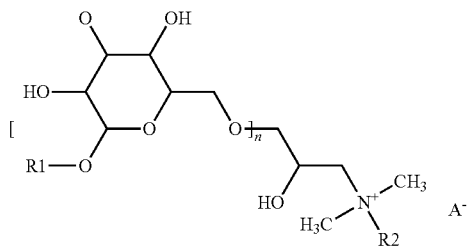

In the above depicted formula the R2 residue stands for a linear or branched C6 to C30 alkyl residue, a linear or branched C6-C30 alkenyl residue, preferably the R residue stands for a residue R selected from: lauryl, myristyl, cetyl, stearyl, oleyl, behenyl or arachidyl.

The R1 residue stands for a linear or branched C6 to C30 alkyl residue, a linear or branched C6-C30 alkenyl residue, preferably the R1 residue stands for a residue selected from: butyl, capryl, caprylyl, octyl, nonyl, decanyl, lauryl, myristyl, cetyl, stearyl, oleyl, behenyl or arachidyl. Even more preferably the R1 residue is selected from industrial mixtures of fatty alcohol fractions of C6/C8 fatty alcohols, C8/C10 fatty alcohols, C10/C12 fatty alcohols, C12/C14 fatty alcohols, C12/C18 fatty alcohols, and most preferably in this regard those industrial fatty alcohol fractions that are of vegetal origin. The index n stands for a number between 1 and 20, preferably between 1 and 10, more preferably between 1 and 5 and most preferably between 1 and 3. The counter ion to the cationic charge $A^-$ is a physiologically acceptable anion, for example halide, methosulfate, phosphate, citrate, tartrate, etc. The counter ion is preferably a halide, such as fluoride, chloride, bromide or methosulfate. The chloride anion is most preferred.

Exemplary particularly preferred cationic alkyl oligoglucosides are the compounds with the INCI names Laurdimoniumhydroxypropyl Decylglucosides Chloride, Laurdimoniumhydroxypropyl Laurylglucosides Chloride, Stearyldimoniumhydroxypropyl Decylglucosides Chloride, Stearyldimoniumhydroxypropyl Laurylglucosides Chloride, Stearyldimoniumhydroxypropyl Laurylglucosides Chloride or Cocoglucosides Hydroxypropyltrimonium Chloride.

Such compounds can be obtained for example under the name Suga® Quat from Colonial Chemical Inc.

The cationic alkyl oligoglucosides are used in a total amount of 0.01 to 10.0 wt %, preferably 0.05 to 5.0 wt %, more preferably 0.1 to 3.0 wt % and most preferably in amounts of 0.2 to 2.0 wt %, each relative to the total weight of the composition. More mixtures of cationic alkyl oligoglucosides may, of course, also be inventively used. In this case it, is preferred to use simultaneously a long chain and a short chain cationic alkyl oligoglucoside.

A quite particularly preferred cationic polymer according to the invention is the copolymer of N-vinyl pyrrolidone, N-vinyl caprolactam, N-(3-dimethylaminopropyl)methacrylamide and 3-(methacryloylamino)propyl-lauryl-dimethylammonium chloride (INCI name: polyquaternium-69), marketed for example by the ISP company under the trade name AquaStyle® 300 (28-32 wt. % active substance in an ethanol-water mixture, molecular weight 350 000).

Further preferred cationic polymers are, for example
cationized honey, for example the commercial product Honeyquat® 50,
polymeric dimethyldiallylammonium salts and their copolymers with esters and amides of acrylic acid and methacrylic acid. The commercially available products Merquat®100 (poly(dimethyldiallylammonium chloride)) and Merquat®550 (dimethyldiallylammonium chloride-acrylamide copolymer) are examples of such cationic polymers with the INCI name polyquaternium-7,
vinyl pyrrolidone-vinyl imidazolium methochloride copolymers, as are offered under the trade names Luviquat® FC 370, FC 550 and the INCI name polyquaternium-16 as well as FC 905 and HM 552,
quaternized vinyl pyrrolidone/dimethylaminoethyl methacrylate, for example vinyl pyrrolidone/dimethylaminoethyl methacrylate methosulfate copolymer, which is marketed under the trade names Gafquat® 755 N and Gafquat® 734 by Gaf Co., USA and the INCI name polyquaternium-11,
quaternized polyvinyl alcohol,
as well as the polymers containing quaternary nitrogen atoms in the main polymer chain, known under the names polyquaternium-2, polyquatemium-17, polyquaternium-18 and polyquaternium-27,
vinyl pyrrolidone-vinyl caprolactam-acrylate terpolymers with acrylic acid esters and acrylamides as the third monomer moieties, as are commercially available, for example, under the trade name Aquaflex® SF 40.

Amphoteric polymers according to the invention are those polymers, in which a cationic group is derived from at least one of the following monomers:
(i) Monomers with quaternary ammonium groups of the general Formula (Mono1),

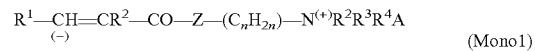

in which $R^1$ and $R^2$ independently of each other stand for hydrogen or a methyl group and $R^3$, $R^4$ und and $R^5$ independently of one another for alkyl groups with 1 to 4 carbon atoms, Z for an NH-group or an oxygen atom, n for a whole number from 2 to 5 and AO is the anion of an organic or inorganic acid,
(ii) Monomers with quaternary ammonium groups of the general Formula (Mono2),

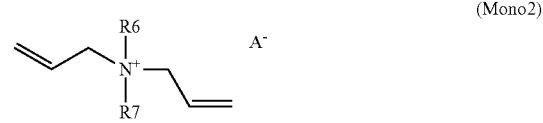

in which $R^6$ and $R^7$ stand independently of one another for a (C1 to C4) alkyl group, in particular for a methyl group and
A" is the anion of an organic or inorganic acid,
(iii) monomeric carboxylic acids of the general Formula (Mono3),

in which $R^8$ and $R^9$, independently of one another are hydrogen or methyl groups.

Particularly preferred are such polymers, which incorporate monomers of type (i), in which $R^3$, $R^4$ and $R^5$ are methyl groups, Z is an NH group and $A^{(-)}$ is a halide, methoxysulfate or ethoxysulfate ion; acrylamidopropyltrimethylammonium chloride is a particularly preferred monomer (i). Acrylic acid is preferably used as the monomer (ii) in the cited polymers.

Particularly preferred amphoteric polymers are copolymers of at least one monomer (Mono1) or (Mono2) with the monomer (Mono3), in particular copolymers of the monomers (Mono2) and (Mono3). Inventively quite particularly preferably used amphoteric polymers are copolymers of diallyldimethylammonium chloride and acrylic acid. These copolymers are marketed under the INCI name polyquaternium-22 inter alia with the trade name Merquat® 280 (Nalco).

Moreover, the amphoteric polymers according to the invention can additionally comprise, besides a monomer (Mono1) or (Mono2) and a monomer (Mono3), a monomer (Mono4)
(iv) monomeric carboxylic acid amides of the general Formula (Mono4),

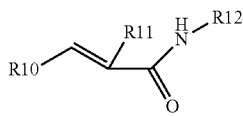

in which $R^{10}$ and $R^{11}$ independently of one another are hydrogen or methyl groups and $R^{12}$ stands for a hydrogen atom or a ($C_1$- to $C_8$) alkyl group.

Inventively quite particularly preferably used amphoteric polymers based on a comonomer (Mono4) are terpolymers of diallyldimethylammonium chloride, acrylamide and acrylic acid. These copolymers are marketed under the INCI name polyquaternium-39 inter alia with the trade name Merquat® Plus 3330 (Nalco).

According to the invention, the amphoteric polymers can be both added directly as well as in salt form, the latter being obtained by neutralization of the polymer with an alkali metal hydroxide, for example.

The abovementioned cationic polymers can be used individually or together in any combination, wherein amounts between 0.01 to 10 wt %, preferably in amounts of 0.01 to 7.5 wt % and quite particularly preferably in amounts of 0.1 to 5.0 wt % are comprised. In this regard, the best results of all are obtained with amounts of 0.1 to 3.0 wt %, each relative to the total composition of the relevant agent.

Of course the hair treatment agents according to the invention also comprise, besides the active substance combination according to the invention, additional ingredients that are usual in cosmetic compositions. The choice of these ingredients is generally guided according to the intended use of the hair treatment agent. In the case of a shampoo, additional surface-active substances are comprised, for example. In the case of hair cures, additional cationic compounds and additional care products are optionally comprised.

As further ingredients, silicones can be particularly advantageously used in the active substance combination according to the invention. In this regard, the preferred silicone is selected from the amino-functional silicones, the Dimethicones, the Dimethiconols, the water-soluble silicones, the cyclomethicones as well as any mixtures of these silicones.

Cationic silicone oils that are inventively suitable are for example the commercially available products Dow Corning (DC) 929 Emulsion, DC 2-2078, DC 5-7113, SM-2059 (General Electric) and SLM-55067 (Wacker).

Particularly preferred inventive agents are characterized in that they comprise at least one amino-functional silicone with the INCI Declaration Trimethylsilylamodimethicone. These are available for example under the trade name Q2-7224 (manufacturer: Dow Corning; a stabilized Trimethylsilylamodimethicon).

Particularly preferred are also agents according to the invention which comprise an amino-functional silicone of the INCI Declaration Amodimethicone or a functionalized Amodimethicone, such as for example Bis(C13-15 Alkoxy) PG Amodimethicone (available for example as the commercial product: DC 8500 from Dow Corning).

Suitable diquaternary silicones are selected from compounds of the general Formula (Si3c)

wherein the R1 to R6 residues independently of each other mean C1 to C22 alkyl residues that can comprise hydroxy groups and wherein preferably at least one of the residues possesses at least 8 carbon atoms and the other residues possess 1 to 4 carbon atoms,
the R7 to R12 residues independently of each other are the same or different and mean C1 to C10 alkyl or phenyl, A means a divalent organic linking group,
n is a number from 0 to 200, preferably from 10 to 120, particularly preferably from 10 to 40, and $X^-$ is an anion.
The divalent linking group is preferably a C1 to C12 alkylene or alkoxyalkylene group that can be substituted with one or more hydroxy groups.
The —$(CH_2)_3$—O—$CH_2$—CH(OH)—$CH_2$— group is particularly preferred.
The anion $X^-$ can be a halide ion, an acetate, an organic carboxylate or a compound of the general Formula $RSO_3^-$, in which R means a C1 to C4 alkyl residue.

A preferred diquaternary silicone has the general Formula (Si3d)

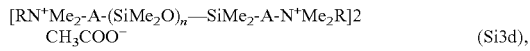

wherein A is the group —$(CH_2)_3$—O—$CH_2$—CH(OH)—$CH_2$—,
R is an alkyl residue containing at least 8 carbon atoms and n is a number from 10 to 120.

Suitable silicone polymers containing two terminal, quaternary ammonium groups are known under the INCI name Quaternium-80. This refers to dimethylsiloxanes containing two terminal trialkylammonium groups. Such diquaternary polydimethylsiloxanes are marketed by Evonik under the trade names AM® Quat 3270, 3272 and 3474.

Inventively preferred hair treatment agents are characterized in that they comprise, based on their weight, 0.01 to 10 wt %, preferably 0.1 to 8 wt %, particularly preferably 0.1 to 7.5 wt % and particularly 0.2 to 5 wt % aminofunctional silicone (s) and/or diquaternary silicone.

Polyammonium-polysiloxane compounds are another amino-functional silicone according to the invention. The polyammonium-polysiloxane compounds can be obtained for example under the trade name Baysilone® from GE Bayer Silicones. In this regard, the products with the trade names Baysilone TP 3911, SME 253 and SFE 839 are preferred. The use of Baysilone TP 3911 is quite particularly preferred as the active component of the composition according to the invention. The polyammonium-polysiloxane compounds are used in the compositions according to the invention in an amount of 0.01 to 10 wt %, preferably 0.01 to 7.5 wt %, particularly preferably 0.01 to 5.0 wt %, quite particularly preferably 0.05 to 2.5 wt % each relative to the total composition.

EP 1887024 A1 describes novel cationic amino-functional silicones that improve in particular the gloss in agents for the care of surfaces, for example human hair. These cationic silicone polymers are characterized in that they possess a silicone backbone as well as at least one polyether moiety and additionally at least one moiety with an ammonium structure. In the context of the present invention, besides the compounds of the abovementioned EP 1887024 A1, the exemplary preferred cationic silicone polymers are in particular the compounds with the INCI names: Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-22 as well as Silicone Quaternium-2 Panthenol Succinate and Silicone Quaternium-16/Glycidyl Dimethicone Crosspolymer. Silicone Quaternium-22 in particular is the most preferred. This raw material is marketed for example by Evonik under the trade name Abil® T-Quat 60. A last inventively particularly preferred amino silicone corresponds to the following formula:

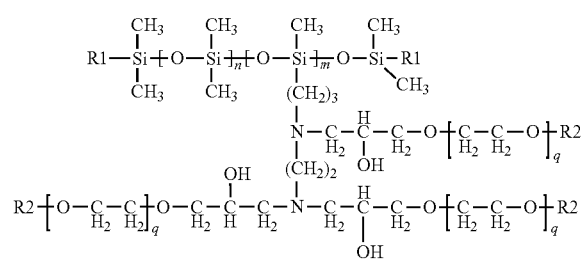

in which R1 stands for a methyl, ethyl, hydroxy, methoxy or ethoxy group,

R2 stands for a straight chain or branched C8 to C24 alkyl or alkylene residue, preferably a straight chain or branched C9 to C22 alkyl or alkylene residue, particularly preferably a straight chain or branched C11 to C18 alkyl or alkylene residue, most preferably a corresponding alkyl residue, n and m each stand for whole numbers from 1 to 1000 and q stands for a whole number from 2 to 50, preferably 4 to 30, particularly preferably 4 to 18 and most preferably from 4 to 12.

The molecular weight of such compounds is 15 000 to 2 000 000, measured with a Brookfield rotation viscosimeter RV, spindle 5, at 20° C. The molecular weight is preferably 30 000 to 1 750 000 and particularly preferably 50 000 to 1 500 000. The nitrogen content of the silicones according to the invention is 0.03 to 4.2 wt %, preferably 0.1 to 2.8 wt % and most preferably 0.16 to 1.4 wt %. Amino-functional cationic silicones according to the invention of the above formula can be obtained from Clariant for example. An inventively most preferred product is commercially available under the INCI name Trideceth-9-Amodimethicone and Trideceth-12.

The cationic amino-functional silicone polymers of the above described formula are comprised in the compositions according to the invention in amounts of 0.01 to 5 wt %, preferably in amounts of 0.05 to 5 wt % and quite particularly preferably in amounts of 0.1 to 5 wt %. In this regard, the best results of all are obtained with amounts of 0.1 to 2.5 wt %, each relative to the total composition of the relevant agent.

The cationic amino-functional silicone polymers are comprised in the compositions according to the invention in amounts of 0.01 to 10 wt %, preferably in amounts of 0.05 to 10 wt % and quite particularly preferably in amounts of 0.1 to 7.5 wt %. In this regard, the best results of all are obtained with amounts of 0.1 to 5 wt %, each relative to the total composition of the relevant agent.

The Dimethicones according to the invention can be linear as well as branched as well as cyclic or cyclic and branched. The viscosities range between 100 and 10 000 000 cPs, measured at 25° C. with a glass capillary viscosimeter following the Dow Corning Corporate Test Method CTM 0004 of 20 Jul. 1970. Preferred viscosities are between 1000 and 5 000 000 cPs, quite particularly preferred viscosities are between 10 000 and 3 000 000 cPs. The most preferred range is between 50 000 and 2 000 000 cPs. Most highly preferred viscosities are in the region of about 60 000 cPs. As an example, reference may be made to the product "Dow Corning 200 with 60000 cSt".

Particularly preferred cosmetic or dermatological preparations according to the invention are characterized in that they comprise at least one silicone of the Formula (Si1.2)

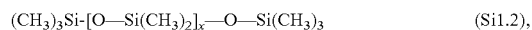

(Si1.2), in which x stands for a number from 0 to 100, advantageously from 0 to 50, more preferably from 0 to 20 and especially 0 to 10.

The Dimethicones are comprised in the compositions according to the invention in amounts of 0.01 to 10 wt %, preferably 0.01 to 8 wt %, particularly preferably 0.1 to 7.5 wt % and in particular 0.1 to 5 wt %, relative to the total composition.

Finally, the silicone compounds are understood to include the Dimethiconols. The Dimethiconols according to the invention can be linear as well as branched as well as cyclic or cyclic and branched. The viscosities range between 100 and 10 000 000 cPs, measured at 25° C. with a glass capillary viscosimeter following the Dow Corning Corporate Test Method CTM 0004 of 20 Jul. 1970. Preferred viscosities are between 1000 and 5 000 000 cPs, quite particularly preferred viscosities are between 10 000 and 3 000 000 cPs. The most preferred range is between 50 000 and 2 000 000 cPs.

The following commercial products are given as examples of such products: Dow Corning 1-1254 Fluid, Dow Corning 2-9023 Fluid, Dow Corning 2-9026 Fluid, Abil OSW 5 (Degussa Care Specialties), Dow Corning 1401 Fluid, Dow Corning 1403 Fluid, Dow Corning 1501 Fluid, Dow Corning 1784 HVF Emulsion, Dow Corning 9546 Silicone Elastomer Blend, SM555, SM2725, SM2765, SM2785 (all four from GE Silicones), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all from Wacker-Chemie GmbH).

The Dimethiconols are comprised in the compositions according to the invention in amounts of 0.01 to 10 wt %, preferably 0.01 to 8 wt %, particularly preferably 0.1 to 7.5 wt % and in particular 0.1 to 5 wt % of Dimethiconol, relative to the composition.

The addition of cyclic Dimethicones, designated by INCI as Cyclomethicones, is also inventively preferred. Here, preferred cosmetic or dermatological preparations according to the invention comprise at least one silicone of the Formula (Si-4)

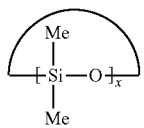 (Si-4)

in which x stands for a number from 3 to 200, advantageously from 3 to 10, more preferably from 3 to 7 and especially 3, 4, 5 or 6.

Likewise inventively preferred agents are characterized in that they comprise at least one silicone of the Formula (Si-5)

in which R stands for the same or different residues from the group H, phenyl, benzyl, —CH$_2$—CH(CH$_3$)Ph, the C$_{1-20}$ alkyl residues, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, x and y stand for a number from 0 to 200, preferably from 0 to 10, more preferably from 0 to 7 and especially 0, 1, 2, 3, 4, 5 or 6, and n stands for a number from 0 to 10, preferably from 1 to 8 and particularly for 2, 3, 4, 5, 6.

Besides the Dimethicones, Dimethiconols, Amodimethicones and/or Cyclomethicones according to the invention, the compositions according to the invention can comprise water-soluble silicones as additional silicones.

Suitable hydrophilic silicones are selected for example from the compounds of the Formulas (Si-6) and/or (Si-7). Particularly preferred water-soluble surfactants based on silicone are selected from the group of the Dimethicon copolyols that are preferably alkoxylated, especially polyethoxylated or polypropoxylated.

Dimethicon copolyols are understood to mean inventively preferred polyoxyalkylene-modified dimethylpolysiloxanes of the general Formulas (Si-6) or (Si-7):

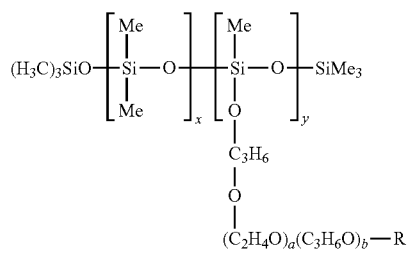 (Si-6)

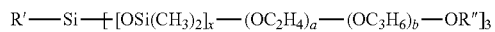 (Si-7)

in which the R residue stands for a hydrogen atom, an alkyl group containing 1 to 12 carbon atoms, an alkoxy group containing 1 to 12 carbon atoms or a hydroxy group; the R' and R" residues mean alkyl groups containing 1 to 12 carbon atoms, x stands for a whole number from 1 to 100, preferably from 20 to 30, y stands for a whole number from 1 to 20, preferably from 2 to 10 and a and b stand for whole numbers from 0 to 50, preferably from 10 to 30.

In the context of the invention, particularly preferred Dimethicon copolyols are for example the commercially marketed products under the trade names SILWET® (Union Carbide Corporation) and DOW CORNING. Inventively particularly preferred Dimethicon copolyols are Dow Corning 190 and Dow Corning 193.

The Dimethicon copolyols are comprised in the compositions according to the invention in amounts of 0.01 to 10 wt %, preferably 0.01 to 8 wt %, particularly preferably 0.1 to 7.5 wt % and in particular 0.1 to 5 wt % of Dimethicon copolyol, relative to the composition. Although all silicones can be used with the active substance combination according to the invention, it has however been shown that the effect decreases in the series amino-functionale silicones, Dimethicones comparable with Dimethiconols, Cyclomethicones and water-soluble silicones. If more than two silicones are used, combinations of amino-functional silicones with Dimethicones and/or Dimethiconols have been shown to be the most effective in increasing the effect. The best effects of all are obtained if each of the already described particularly preferred silicone compounds are used as the silicone compounds.

Another highly preferred ingredient of the compositions according to the invention is a hydroxycarboxylic acid. It was surprisingly observed that in the cases, in which a hydroxycarboxylic acid is additionally added to the inventive ingredients of claims 1 and 2, then the compositions are also significantly more stable in their storage stability. In particular, the stability is significantly improved with higher contents of silicone oils.

Hydroxycarboxylic acids are carboxylic acids that possess at least one carboxylic group as well as at least one hydroxy group in the molecule. The hydroxycarboxylic acids include in particular the so-called AHA acids as well as β-hydroxycarboxylic acids. Another name for such hydroxy acids is fruit acids, because the acids frequently occur in fruit. The hydroxycarboxylic acid according to the invention is selected in particular from glycolic acid, lactic acid, glyceric acid, malic acid, citric acid, isocitric acid, mandelic acid, tartronic acid, tartaric acid, vanillic acid, salicylic acid, mevalonic acid, β-hydroxybutyric acid, gallic acid or protocatechuic acid. The hydroxycarboxylic acid is particularly preferably selected from glycolic acid, lactic acid, glyceric acid, malic acid, citric acid, mandelic acid, tartaric acid, vanillic acid and salicylic acid. The hydroxycarboxylic acid is quite particularly preferably selected from glycolic acid, lactic acid, malic acid, citric acid, mandelic acid, tartaric acid and vanillic acid. The hydroxycarboxylic acid is most preferably selected from malic acid, mandelic acid, tartaric acid and vanillic acid. Mixtures of hydroxycarboxylic acids can of course also be used.

The compositions according to the invention comprise the hydroxycarboxylic acids in a total amount of 0.01 to 15 wt %, in particular 0.01 to 10.0 wt %, preferably 0.1 to 7.5 wt % and most preferably in an amount of 0.1 to 5.0 wt %, each relative to the total composition.

In many cases the compositions comprise at least one surface-active substance, wherein, in principle, not only anionic, but also zwitterionic, ampholytic, non-ionic and cationic surface-active substances are suitable. The choice of the surface active substances depends on the type of the agent.

Suitable anionic surfactants (Tanion) for the inventive preparations are all anionic surface-active materials that are suitable for use on the human body. Typical examples of anionic surfactants are:

linear and branched fatty acids containing 8 to 30 carbon atoms (soaps),
ether carboxylic acids of the formula R—O—(CH$_2$—CH$_2$O)$_x$—CH$_2$—COOH, in which R is a linear alkyl group with 10 to 22 carbon atoms and x=0 or 1 to 16, and their salts,
acyl sarcosides with 8 to 24 carbon atoms in the acyl group,
acyl taurides with 8 to 24 carbon atoms in the acyl group, acyl isethionates with 8 to 24 carbon atoms in the acyl group, mono- and dialkyl esters of sulfosuccinic acid with 8 to 24 carbon atoms in the alkyl group and mono-alkyl polyoxyethyl esters of sulfosuccinic acid with 8 to 24 carbon atoms in the alkyl group and 1 to 6 oxyethylene groups, linear alkane sulfonates containing 8 to 24 carbon atoms, linear alpha-olefin sulfonates containing 8 to 24 carbon atoms, alpha-sulfo fatty acid methyl esters of fatty acids containing 8 to 30 carbon atoms, alkyl sulfates and alkyl polyglycol ether sulfates of the Formula R—O(CH$_2$—CH$_2$O)$_x$—OSO$_3$H, in which R is preferably a linear alkyl group containing 8 to 30 carbon atoms and x=0 or 1 to 12, hydroxysulfonates corresponding essentially to at least one of the two following formulas or to their mixtures as well as to their salts, CH$_3$—(CH$_2$)$_y$—CHOH—(CH$_2$)$_p$—(CH—SO$_3$M)-(CH$_2$),—CH$_2$—O—(C$_n$H$_{2n}$O)$_x$—H, and/or CH$_3$—(CH$_2$)$_y$—(CH—SO$_3$M)-(CH$_2$)$_p$—CHOH—(CH$_2$), —CH$_2$—O—(C$_a$H$_{2n}$O)$_x$—H wherein in both Formulas y and z=0 or whole numbers from 1 to 18, p=0, 1 or 2 and the sum (y+z+p) is a number from 12 to 18, x=0 or a number from 1 to 30 and n is a whole number from 2 to 4 as well as M=H or alkali metal, in particular sodium, potassium, lithium, alkaline earth, in particular magnesium, calcium, zinc and/or an ammonium ion that can optionally be substituted, in particular mono, di, tri or tetraammonium ions with C1 to C4 alkyl, alkenyl or aryl residues, sulfated hydroxyalkyl polyethylene glycol ethers and/or hydroxyalkylene propylene glycol ethers of the Formula R$^1$—(CHOSO$_3$M)-CHR$^3$—(OCHR$^4$—CH$_2$)$_n$—OR$^2$ with R$^1$, a linear alkyl residue with 1 to 24 carbon atoms, R$^2$ for a linear or branched, saturated alkyl residue with 1 to 24 carbon atoms, R$^3$ for hydrogen or a linear alkyl residue with 1 to 24 carbon atoms, R$^4$ for hydrogen or a methyl residue and M for hydrogen, ammonium, alkylammonium, alkanolammonium, in which the alkyl and alkanol residues each have 1 to 4 carbon atoms, or a metal atom selected from lithium, sodium, potassium, calcium or magnesium and n for a number in the range of 0 to 12 and additionally the total number of carbon atoms comprised in R$^1$ and R$^3$ ranges from 2 to 44, sulfonates of unsaturated fatty acids with 8 to 24 carbon atoms and 1 to 6 double bonds, esters of tartaric acid and citric acid with alcohols, which represent the addition products of about 2-15 molecules of ethylene oxide and/or propylene oxide on fatty alcohols containing 8 to 22 carbon atoms, alkyl and/or alkenyl ether phosphates of the Formula, R$^1$(OCH$_2$CH$_2$)$_n$—O—(PO—OX)—OR$^2$, in which R$^1$ preferably stands for an aliphatic hydrocarbon residue containing 8 to 30 carbon atoms, R$^2$ stands for hydrogen, a (CH$_2$CH$_2$O)$_n$R$^2$ residue or X, n for numbers between 1 and 10 and X for hydrogen, an alkali metal or alkaline earth metal or NR$^3$R$^4$R$^5$R$^6$, with R$^3$ to R$^6$, independently of each other standing for a C$_1$ to C$_4$ hydrocarbon residue, sulfated fatty acid alkylene glycol esters of the Formula RCO(AlkO)$_n$SO$_3$M in which RCO— stands for a linear or branched, aliphatic, saturated and/or unsaturated acyl residue with 6 to 22 carbon atoms, Alk for CH$_2$CH$_2$, CHCH$_3$CH$_2$ and/or CH$_2$CHCH$_3$, n for numbers from 0.5 to 5 and M for a metal, such as alkali metals, in particular sodium, potassium, lithium, alkaline earth metals, in particular magnesium, calcium, zinc, or ammonium ion, such as $^+$NR$^3$R$^4$R$^5$R$^6$, with R$^3$ to R$^6$ independently of each other standing for hydrogen or a C1 to C4 hydrocarbon residue, monoglyceride sulfates and monoglyceride ether sulfates of the Formula

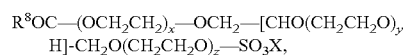

in which R$^8$CO stands for a linear or branched acyl residue containing 6 to 22 carbon atoms, the sum of x, y and z is 0 or stands for numbers between 1 and 30, preferably 2 to 10, and X stands for an alkali metal or alkaline earth metal. In the context of the invention, typical examples of suitable monoglyceride (ether) sulfates are the reaction products of lauric acid monoglyceride, cocoa fatty acid monoglyceride, palmitic acid monoglyceride, stearic acid monoglyceride, oleic acid monoglyceride and tallow fatty acid monoglyceride as well as their ethylene oxide adducts with sulfur trioxide or chlorosulfonic acid in the form of their sodium salts. Preferably, monoglyceride sulfates are employed, in which R$^8$CO stands for a linear acyl residue containing 8 to 18 carbon atoms, amide ether carboxylic acids, R1-CO—NR$^2$—CH$_2$CH$_2$—O—(CH$_2$CH$_2$O)$_n$CH$_2$COOM, with R$^1$ as a straight chain or branched alkyl or alkenyl residue with 2 to 30 carbon atoms in the chain, n stands for a whole number of 1 to 20 and R$^2$ stands for hydrogen, a methyl, ethyl, propyl, isopropyl, n-butyl, t-butyl or isobutyl residue and m stands for hydrogen or for a metal, such as alkali metals, in particular sodium, potassium, lithium, alkaline earth metals, in particular magnesium, calcium, zinc, or an ammonium ion, such as $^+$NR$^3$R$^4$R$^5$R$^6$, with R$^3$ to R$^6$ independently of each other standing for hydrogen or a C1 to C4 hydrocarbon residue. Such products are available for example from Chem-Y under the product name Akypo®.

acyl glutamates of the Formula XOOC—CH2CH2CH(C(NH)OR)—COOX, in which RCO stands for a linear or branched acyl residue with 6 to 22 carbon atoms and 0 and/or 1, 2 or 3 double bonds and X stands for hydrogen, an alkali metal and/or alkaline earth metal, ammonium, alkylammonium, alkanolammonium or glucammonium, condensation products of a water-soluble salt of a water-soluble albumin hydrolysate with a C8-C30 fatty acid. Such products have long been commercially available under the trade names Lamepon®, Maypon®, Gluadin®, Hostapon® KCG or Amisoft®.

carboxylates, sulfates, phosphates of alkyl and/or alkenyl oligoglycosides and/or isethionates, acyl lactylates and hydroxy mixed ether sulfates.

In so far as the mild anionic surfactants comprise polyglycol ether chains, the latter quite particularly preferably have a narrow homolog distribution. Furthermore, in the case of mild anionic surfactants with polyglycol ether units, the number of the glycol ether groups is preferably 1 to 20, preferably 2 to 15, particularly preferably 2 to 12. Particularly mild anionic surfactants with polyglycol ether groups without restricted homolog distribution can also be obtained for example if on the one hand the number of the polyglycol ether groups is 4 to 12 and Zn or Mg ions are selected as the counter ion. An example of this is the commercial product Texapon® ASV.

Particularly suitable zwitterionic surfactants are the so-called betaines such as the N-alkyl-N,N-dimethylammonium glycinates, for example the cocoalkyldimethylammonium glycinate, N-acylaminopropyl-N,N-dimethylammonium glycinates, for example the cocoacylaminopropyldimethylammonium glycinate, and 2-alkyl-3-carboxymethyl-3-hydroxyethyl imidazolines with 8 to 18 carbon atoms in each of the alkyl or acyl groups, as well as cocoacylaminoethyl hydroxyethyl carboxymethyl glycinate. A preferred zwitterionic surfactant is the fatty acid amide derivative, known under the INCI name Cocamidopropyl Betaine.

Ampholytic surfactants (Tampho) are understood to mean those surface-active compounds that are capable of forming inner salts. Examples of suitable ampholytic surfactants are N-alkyl glycines, N-alkylamino propionic acids, N-alkylamino butyric acids, N-alkylimino dipropionic acids, N-hydroxyethyl-N-alkylamidopropylglycine, N-alkyl taurines, N-alkyl sarcosines, 2-alkylamino propionic acids and alkylamino acetic acids, each with about 8 to 24 carbon atoms in the alkyl group. Typical examples of amphoteric or zwitterionic surfactants are alkyl betaines, alkylamido betaines, amino propionates, amino glycinates, imidazolinium betaines and sulfo betaines. Particularly preferred ampholytic surfactants are N-cocoa alkylamino propionate, cocoa acylaminoethylamino propionate and $C_{12}$-$C_{18}$ acyl sarcosine.

Non-ionic surfactants (Tnio) are for example
- addition products of 2 to 50 mol ethylene oxide and/or 0 to 5 mol propylene oxide to linear and branched fatty alcohols containing 6 to 30 carbon atoms, the fatty alcohol polyglycol ethers or the fatty alcohol polypropylene glycol ethers or mixed fatty alcohol polyethers,
- addition products of 2 to 50 mol ethylene oxide and/or 0 to 5 mol propylene oxide to linear and branched fatty acids containing 6 to 30 carbon atoms, the fatty acid polyglycol ethers or the fatty acid polypropylene glycol ethers or mixed fatty acid polyethers,
- addition products of 2 to 50 mol ethylene oxide and/or 0 to 5 mol propylene oxide to linear and branched alkylphenols containing 8 to 15 carbon atoms in the alkyl group, the alkylphenol polyglycol ethers or the alkylphenol polypropylene glycol ethers or mixed alkylphenol polyethers,
- methyl or C2-C6 alkyl residue end blocked addition products of 2 to 50 mol ethylene oxide and/or 0 to 5 mol propylene oxide to linear and branched fatty alcohols with 8 to 30 carbon atoms, to fatty acids with 8 to 30 carbon atoms and to alkylphenols with 8 to 15 carbon atoms in the alkyl group, such as, for example, the available types under the sales names Dehydrol® LS, Dehydrol® LT (Cognis),
- $C_{12}$-$C_{30}$ fatty acid mono and diesters of addition products of 1 to 30 mol ethylene oxide to glycerin,
- addition products of 5 to 60 mol ethylene oxide to castor oil and hydrogenated castor oil, polyol esters of fatty acids, such as, for example, the commercial product Hydagen® HSP (Cognis) or Sovermol types (Cognis),
- alkoxylated triglycerides,
- alkoxylated fatty acid alkyl esters of the Formula (Tnio-1)

$$R^1CO-(OCH_2CHR^2)_wOR^3 \qquad \text{(Tnio-1)}$$

in which $R^1CO$ stands for a linear or branched, saturated and/or unsaturated acyl residue containing 6 to 22 carbon atoms, $R^2$ for hydrogen or methyl, $R^3$ for linear or branched alkyl residues containing 1 to 4 carbon atoms and w for numbers from 1 to 20,

- amine oxides,
- hydroxy mixed ethers,  with $R^1$ standing for a linear or branched, saturated or unsaturated alkyl and/or alkenyl residue containing 2 to 30 carbon atoms, $R^2$ stands for hydrogen, a methyl, ethyl, propyl or isopropyl residue, $R^3$ stands for a linear or branched alkyl residue containing 2 to 30 carbon atoms, x stands for 0 or a number from 1 to 20, y for a number from 1 to 30 and z stands for the number 1, 2, 3, 4 or 5.
- sorbitol esters of fatty acids and addition products of ethylene oxide to sorbitol esters of fatty acids such as e.g. the polysorbates,
- sugar esters of fatty acids and addition products of ethylene oxide to sugar esters of fatty acids,
- addition products of ethylene oxide to fatty acid alkanolamides and fatty amines,
- sugar surfactants of the alkyl and alkenyl oligoglycosides type,
- sugar surfactants of the fatty acid N-alkylpolyhydroxyalkylamide type,
- fatty acid amide polyglycol ethers, fatty amine polyglycol ethers,
- mixed ethers or mixed formals and polysorbates.

The surfactants are used in quantities of 0.05 to 45 wt %, preferably 0.1 to 30 wt % and quite particularly preferably from 0.5-25 wt %, based on the total inventively used composition.

Exemplary inventively usable emulsifiers are
- addition products of 4 to 30 mol ethylene oxide and/or 0 to 5 mol propylene oxide to linear fatty alcohols containing 8 to 22 carbon atoms, to fatty acids containing 12 to 22 carbon atoms and to alkyl phenols containing 8 to 15 carbon atoms in the alkyl group,
- $C_{12}$-$C_{22}$ fatty acid mono- and diesters of addition products of 1 to 30 mol ethylene oxide on polyols containing 3 to 6 carbon atoms, especially on glycerin,
- ethylene oxide- and polyglycerin-addition products on methyl glucoside fatty acid esters, fatty acid alkanolamides and fatty acid glucamides,
- $C_8$-$C_{22}$ alkyl mono and oligoglycosides and their ethoxylated analogs, wherein the degrees of oligomerization are 1.1 to 5, particularly 1.2 to 2.0, and glucose as the sugar component are preferred,
- mixtures of alkyl(oligo)glucosides and fatty alcohols, for example the commercial product Montanov® 68,
- addition products of 5 to 60 mol ethylene oxide onto castor oil and hydrogenated castor oil,
- partial esters of polyols containing 3-6 carbon atoms with saturated fatty acids containing 8 to 22 carbon atoms,
- sterols, both from animal tissue (zoosterols, cholesterols, lanosterols) as well as from vegetal fats (phytosterols, ergosterol, stigmasterol, sitosterol) or from fungi and yeasts (mycosterols),
- phospholipids (lecithines, phosphatidyl cholines),
- fatty acid esters of sugars and sugar alcohols, such as sorbitol,
- polyglycerins and polyglycerin derivatives such as for example polyglycerin poly-12-hydroxystearate (commercial product Dehymuls® PGPH).

The inventive agents preferably comprise the emulsifiers in quantities of 0.1 to 25 wt %, particularly 0.5-15 wt %, based on the total composition.

The compositions according to the invention particularly preferably comprise fats as the additional active principle. Fats are understood to mean fatty acids, fatty alcohols, natural and synthetic waxes that can exist both in solid form as well as liquid in aqueous dispersion, and natural and synthetic cosmetic oil components. Linear and/or branched, saturated and/or unsaturated fatty acids having 6-30 carbon atoms can be used as the fatty acids. Fatty acids having 10-22 carbon atoms are preferred. Among these may be cited the isostearic acids, such as the commercial products Emersol® 871 and Emersol® 875, and isopalmitic acids such as the commercial product Edenor® IP 95, as well as all other fatty acids commercialized under the trade names Edenor® (Cognis). Further typical examples of such fatty acids are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures. Usually, the fatty acid fractions obtainable from coconut oil and palm oil are particularly preferred; in general, the addition of stearic acid is particularly preferred.

The addition quantity ranges from 0.1-15 wt %, based on the total agent. The quantity preferably ranges from 0.5-10 wt %, wherein quantities of 1-5 wt can be quite particularly advantageous.

Saturated, mono or polyunsaturated, branched or linear fatty alcohols containing $C_6$ to $C_{30}$, preferably $C_{10}$ to $C_{22}$ and quite particularly preferably $C_{12}$ to $C_{22}$ carbon atoms can be employed as the fatty alcohols. In the scope of the invention, decanol, octanol, octenol, dodecenol, decenol, octadienol, dodecadienol, decadienol, oleyl alcohol, eruca alcohol, ricinyl alcohol, stearyl alcohol, isostearyl alcohol, cetyl alcohol, lauryl alcohol, myristyl alcohol, arachidyl alcohol, capryl alcohol, caprinic alcohol, linalyl alcohol, linolenyl alcohol and behenyl alcohol, as well as the Guerbet alcohols can be added, this listing being intended as exemplary and not limiting in character. However, the fatty alcohols are preferably derived from naturally occurring fatty acids, usually obtained by reducing the fatty acid esters. Those fatty alcohol fractions that represent a mixture of different fatty alcohols are likewise inventively employable. Such substances can be bought, for example, under the trade names Stenol®, e.g. Stenol® 1618 or Lanette®, e.g. Lanette® 0 or Lorol®, e.g. Lorol® C8, Lorol® C14, Lorol® C18, Lorol® C8-18, HD-Ocenol®, Crodacol®, e.g. Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. Of course, wool wax alcohols such as those that are commercially available for example, under the trade names Corona®, White Swan®, Coronet® or Fluilan® can also be inventively added. The fatty alcohols are added in quantities of 0.1-30 wt %, based on the total preparation, preferably in quantities of 0.1-20 wt %.

According to the invention, solid paraffins or isoparaffins, carnuba wax, beeswax, candelilla wax, ozocerite, ceresine, sperm wax, sunflower wax, fruit waxes such as for example apple wax or citrus wax, microwaxes of PE or PP can be added as the natural or synthetic waxes. These types of waxes are available, for example, from Kahl & Co., Trittau.

The added quantities are 0.1 to 50 wt %, based on the total composition, preferably 0.1 to 20 wt % and particularly preferably 0.1 to 15 wt %, based on the total composition.

The total amount of oil and fat components in the inventive agents is normally 0.5-75 wt %, based on the total agent. Quantities of 0.5 to 35 wt % are inventively preferred.

Another inventive synergistic active principle in the compositions according to the invention with the active principle complex are protein hydrolysates and/or their derivatives.

According to the invention, the added protein hydrolysates can be of both vegetal as well as animal or marine or synthetic origin.

Animal protein hydrolysates are, for example, elastin, collagen, keratin, silk protein, and milk albumin protein hydrolysates, which can also be present in the form of their salts. Such products are marketed, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

Furthermore, inventively preferred vegetal protein hydrolyzates are for example soya, almond, pea, potato, moring a and wheat protein hydrolyzates. Such products are available, for example, under the trade names Gluadin® (Cognis), DiaMin® (Diamalt), Lexein® (Inolex) Hydrosoy® (Croda), Hydrolupin® (Croda), Hydrosesame® (Croda), Hydrotritium® (Croda), Crotein® (Croda) and Puricare® LS 9658 from Laboratoires Serobiologiques. Additional inventively preferred protein hydrolysates are of marine origin. These include for example collagen hydrolysates of fish or algae as well as protein hydrolysates of mussels or pearl hydrolysates. Examples of pearl extracts according to the invention are the commercial products Pearl Protein Extract BG® or Crodarom® Pearl.

In addition, cationized protein hydrolysates are considered as protein hydrolysates, wherein the base protein hydrolysate can originate from animals, for example from collagen, milk or keratin, from plants, for example from wheat, maize, rice, potatoes, soya or almonds, from marine life, for example from fish collagen or algae, or from biotechnologically obtained protein hydrolysates. Typical examples of inventive cationic protein hydrolysates and derivatives are the commercially available products and those cited under the INCI names in the "International Cosmetic Ingredient Dictionary and Handbook", (seventh edition 1997, The Cosmetic, Toiletry, and Fragrance Association 1101 17$^{th}$ Street, N. W., Suite 300, Washington, D.C. 20036-4702). The compositions comprise the protein hydrolysates in concentrations of 0.001 wt. % to 20 wt. %, preferably 0.05 wt. % up to 15 wt. % and quite particularly preferably in amounts of 0.05 wt. % up to 5 wt. %.

Vitamins, provitamins or vitamin precursors are a further preferred group of ingredients of the inventive compositions with the inventive active principle complex. Here, vitamins, provitamins and vitamin precursors which are assigned to the groups A, B, C, E, F and H are particularly preferred.

The group of substances designated as vitamin A includes retinol (vitamin $A_1$) as well as 3,4-didehydroretinol (vitamin $A_2$). β-Carotene is the provitamin of retinol. Examples of suitable vitamin A components according to the invention are vitamin A acid and its esters, vitamin A aldehyde and vitamin A alcohol as well as its esters such as the palmitate and acetate. The agents according to the invention preferably comprise the vitamin A components in amounts of 0.05 to 1 wt %, based on the total preparation.

The vitamin B group or the vitamin B complex include inter alia:
Vitamin $B_1$ (Thiamin)
Vitamin $B_2$ (Riboflavin)
Vitamin $B_3$. The compounds nicotinic acid and nicotinamide (niacinamide) are often included under this designation. According to the invention, nicotinamide is preferred and is comprised of 0.05 to 1 wt %, based on the total agent.
Vitamin $B_5$ (pantothenic acid, panthenol and pantolactone). In the context of this group, panthenol and/or pantolactone is preferably used. Useable derivatives of panthenol according to the invention are especially the esters and ethers of panthenol as well as cationically derivatized panthenols. Specific representatives are for example, panthenol triacetate, panthenol monoethyl ether and its monoacetate as well as cationic panthenol derivatives.

In the present invention, pantothenic acid is preferably employed as a derivative in the form of the stabilized calcium salt and sodium salt (Ca pantothenate, Na pantothenate).

Vitamin $B_6$ (pyridoxine as well as pyridoxamine and pyridoxal).

The cited compounds of the vitamin B type, in particular vitamin $B_3$, $B_5$ and $B_6$, are preferably comprised in the agents according to the invention in amounts of 0.05 to 10 wt %, based on the total agent. Quantities of 0.1 to 5 wt % are particularly preferred.

Vitamin C (ascorbic acid). Vitamin C is preferably added to the agents according to the invention in amounts of 0.1 to 3 wt %, based on the total agent. Its use in the form of the palmitate ester, the glucosides or phosphates can be preferred. The use in combination with tocopherols can also be preferred.

Vitamin E (Tocopherols, especially α-tocopherol). Tocopherol and its derivatives, among which are particularly included the esters such as the acetate, the nicotinate, the phosphate and the succinate, are used in the agents according to the invention preferably comprised in amounts of 0.05-1 wt %, based on the total agent.

Vitamin F. The term "vitamin F" is usually taken to mean essential fatty acids, particularly linoleic acid, linolenic acid and arachidonic acid.

Vitamin H. The compound (3aS,4S,6aR)-2-oxohexahydrothienol[3,4-d]imidazole-4-valeric acid denotes Vitamin H, for which the trivial name biotin has become accepted. The agents according to the invention preferably comprise biotin in amounts of 0.0001 to 1.0 wt %, particularly in amounts of 0.001 to 0.01 wt %.

The compositions according to the invention preferably comprise vitamins, provitamins and vitamin precursors from the groups A, B, E and H. Panthenol, pantolactone, pyridoxine and its derivatives as well as nicotinamide and biotin are especially preferred.

A particularly preferred group of ingredients in the cosmetic compositions according to the invention are the betaines cited below: carnitine, carnitine tartrate, carnitine magnesium citrate, acetylcarnitine, betalaine, 1,1-dimethylproline, choline, choline chloride, choline bitartrate, choline dihydrogen citrate and the compound N,N,N-trimethylglycine cited in the literature as a betaine.

Carnitine, histidine, choline as well as betaine are preferably used. In a particularly preferred embodiment of the invention, L-carnitine tartrate is employed as the active principle.

Inventively particularly preferred agents according to the invention comprise, based on their weight, 0.0001 to 10.0 wt %, preferably 0.0005 to 5.0 wt %, particularly preferably 0.001 to 2.0 wt % and particularly 0.001 to 1.0 wt % of at least one of the abovementioned betaines, especially carnitine tartrate.

In another inventively preferred embodiment, the inventive compositions comprise bioquinones. Suitable bioquinones in the inventive agents are understood to include one or more ubiquinones and/or plastoquinones. The preferred ubiquinones according to the invention have the following formula:

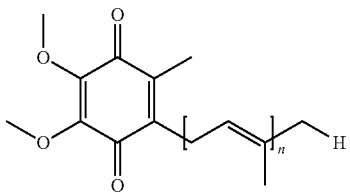

with n=6, 7, 8, 9 or 10.

The coenzyme Q-10 is most preferred here.

Preferred compositions according to the invention comprise purine and/or purine derivatives in narrow quantitative ranges. Inventively preferred cosmetic agents are characterized in that they comprise, based on their weight, 0.001 to 2.5 wt %, preferably 0.0025 to 1 wt %, particularly preferably 0.005 to 0.5 wt % and particularly 0.01 to 0.1 wt % purine and/or purine derivative(s). Inventively preferred cosmetic agents are characterized in that they comprise purine, adenine, guanine, uric acid, hypoxanthine, 6-purinethiol, 6-thioguanine, xanthin, caffeine, theobromine or theophylline. Caffeine is most preferred in hair cosmetic preparations.

In another preferred embodiment of the present invention, the cosmetic agent comprises ectoine ((5)-2-methyl-1,4,5,6-tetrahydro-4-pyrimidine carboxylic acid).

Agents that comprise, based on their weight, 0.00001 to 10.0 wt %, preferably 0.0001 to 5.0 wt % and particularly 0.001 to 3 wt % of the active principles from the group made up of carnitine, coenzyme Q-10, ectoine, a vitamin of the B series, a purine and their derivatives or physiologically representative salts are inventively particularly preferred. A quite particularly preferred care additive in the hair treatment agents according to the invention is taurine. Taurine is understood to mean exclusively 2-aminoethane sulfonic acid and by a derivative the explicitly cited derivatives of taurine. The derivates of taurine are understood to mean N-monomethyltaurine, N,N-dimethyltaurine, taurine lysylate, taurine tartrate, taurine ornithate, lysyltaurine and ornithyltaurine.

Inventively particularly preferred agents according to the invention comprise, based on their weight, 0.0001 to 10.0 wt %, preferably 0.0005 to 5.0 wt %, particularly preferably 0.001 to 2.0 wt % and particularly 0.001 to 1.0 wt % of taurine and/or a derivative of taurine.

Moreover, the action of the compositions according to the invention can be further augmented by a 2-pyrrolidone-5-carboxylic acid and its derivatives. The sodium, potassium, calcium, magnesium or ammonium salts are preferred, in which the ammonium ion carries one to three $C_1$ to $C_4$ alkyl groups besides hydrogen. The sodium salt is quite particularly preferred. The quantities employed in the inventive agents preferably range from 0.05 to 10 wt %, based on the total composition, particularly preferably 0.1 to 5 wt %, and particularly 0.1 to 3 wt %.

The use of plant extracts as the care substances allows the hair treatment agents according to the invention to be formulated particularly in harmony with nature and nevertheless very effectively in regard to their care performance. The otherwise usual preservatives can even be optionally obviated. Above all the inventively preferred extracts are from green tea, oak bark, stinging nettle, hamamelis, hops, henna, camomile, burdock root, field horsetail, hawthorn, linden flowers, almonds, aloe vera, spruce needles, horse chestnut, sandal wood, juniper, coconut, mango, apricot, lime, wheat, kiwi, melon, orange, grapefruit, sage, rosemary, birch, malva, lady's smock, common yarrow, thyme, lemon balm, restharrow, coltsfoot, marshmallow, meristem, ginseng, coffee, cocoa, moringa, ginger and Ayuvedic plant extracts such as for example *Aegle Marmelos* (Bilwa), *Cyperus Rotundus* (Nagar Motha), *Emblica Officinalis* (Amalki), *Morida Citrifolia* (Ashyuka), *Tinospora Cordifolia* (Guduchi), *Santalum album*, (Chandana), *Crocus Sativus* (Kumkuma), *Cinnamonum Zeylanicum* and *Nelumbo Nucifera* (Kamala), sweet grasses like wheat, barley, rye, oats, spelt, maize, the various varieties of millet (sorghum, crabgrass, foxtail millet as examples), sugar cane, meadow fescue, meadow foxtail, oat grass, bent grass, tall grass, moor grass, bamboo, cotton grass, fountain grasses, Andropogonodeae (*Imperata Cylindrica* also called cogon grass), buffalo grass, cord grass, Bermuda grasses, love grass, *Cymbopogon* (lemon grass), Oryzeae (rice), *Zizania* (wild rice), marram grass, blue oat, creeping soft grass, quaking grasses, meadow grasses, wheatgrasses and *Echinacea purpurea* (L.) Moench, all types of wine as well as pericarp of *Litchie chinensis*.

According to the invention, the plant extracts can be used in pure as well as in diluted form. When they are used in diluted form, they normally comprise ca. 2-80 wt % active substance and the solvent is the extraction agent or mixture of extraction agents used for their extraction.

In another embodiment, the compositions according to the invention additionally comprise at least one UV light filter. UVB filters can be oil-soluble or water-soluble.

As oil-soluble substances, the following may be cited, for example:

3-benzylidene camphor, e.g. 3-(4-methylbenzylidene) camphor;

4-aminobenzoic acid derivatives, preferably 2-ethylhexyl 4-(dimethylamino)benzoate, 2-octyl 4-(dimethylamino)benzoate and amyl 4-(dimethylamino)benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (Octocrylene);

esters of salicylic acid, preferably 2-ethylhexyl salicylate, 4-isopropylbenzyl salicylate, homomethyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzmalonic acid, preferably di-2-ethylhexyl 4-methoxybenzmalonate;

triazine derivatives, such as e.g. 2,4,6-trianilino-(p-carbo-2'-ethyl-1'-hexyloxy)-1,3,5-triazine and octyl triazone.

propane-1,3-diones, such as e.g. 1-(4-tert-butylphenyl)-3-(4'-methoxyphenyl)propane-1,3-dione;

The water-soluble substances include:

2-phenylbenzimidazole-5-sulfonic acid and its alkali metal, alkaline earth metal, ammonium, alkylammonium, alkanolammonium and glucammonium salts;

sulfonic acid derivatives of benzophenones, preferably 2-hydroxy-4-methoxybenzophenone-5-sulfonic acid and its salts;

sulfonic acid derivatives of 3-benzylidenecamphor, such as e.g. 4-(2-oxo-3-bornylidenemethyl)benzene sulfonic acid and 2-methyl-5-(2-oxo-3-bornylidene)sulfonic acid and their salts.

In particular, derivatives of benzoylmethane come into consideration as a typical UV-A filter, such as for example 1-(4'-tert-butylphenyl)-3-(4'-methoxyphenyl)propane-1,3-dione or 1-phenyl-3-(4'-isopropylphenyl)-propane-1,3-dione. Naturally, the UV-A and UV-B filters can also be added as mixtures.

Beside the cited soluble materials, insoluble pigments, in particular finely dispersed metal oxides or salts can also be considered for this purpose, such as for example titanium dioxide, zinc oxide, iron oxide, aluminum oxide, cerium oxide, zirconium oxide, silicates (talc), barium sulfate and zinc stearate. These pigments are inventively preferred, in particular as a component of a mixture of a plurality of structurally different UV filters. Here, the particles should have a mean diameter of less than 100 nm, preferably between 5 and 50 nm and especially between 15 and 30 nm. They can be spherical, however elliptical or other non-spherical shaped particles can also be used.

The total amount of UV filter substances in the compositions according to the invention is, each relative to the total composition, 0.01 to 15.0 wt %, preferably 0.01 to 10.0 wt %, particularly preferably 0.2 to 10.0 wt % and most preferably 0.3 to 10.0 wt %.

Occasionally, it may be required to use anionic polymers. Exemplary anionic monomers, from which such polymers can be made, are acrylic acid, methacrylic acid, crotonic acid, maleic anhydride and 2-acrylamido-2-methylpropane sulfonic acid. Here, the acidic groups may be fully or partially present as the sodium, potassium, ammonium, mono or triethanolammonium salt. Preferred monomers are 2-acrylamido-2-methylpropane sulfonic acid and acrylic acid.

Anionic polymers that comprise 2-acrylamido-2-methylpropane sulfonic acid alone or as the comonomer, have proven to be quite particularly effective; the sulfonic acid group may be fully or partially present as the sodium, potassium, ammonium, mono- or triethanolammonium salt.

The homopolymer of 2-acrylamido-2-methylpropane sulfonic acid, which is commercially available, for example under the trade name Rheothik® 11-80, is particularly preferred.

Preferred non-ionic monomers are acrylamide, methacrylamide, acrylic acid esters, methacrylic acid esters, vinyl pyrrolidone, vinyl ethers and vinyl esters.

Preferred anionic copolymers are acrylic acid-acrylamide copolymers and particularly polyacrylamide copolymers with monomers that contain sulfonic acid groups. Such a polymer is comprised in the commercial product Sepigel®305 from the SEPPIC company.

Likewise preferred anionic homopolymers are uncrosslinked and crosslinked polyacrylic acids. Preferred crosslinking agents can be allyl ethers of pentaerythritol, of sucrose and of propylene. Such compounds are commercially available under the trade name Carbopol®, for example.

Copolymers of maleic anhydride and methyl vinyl ether, especially those with crosslinks are also color-conserving polymers. A maleic acid-methyl vinyl ether copolymer crosslinked with 1,9-decadiene is commercially available under the trade name Stabileze® QM. The compositions according to the invention preferably comprise the anionic polymers in quantities of 0.05 to 10 wt %, based on the total composition. Quantities of 0.1 to 5 wt % are particularly preferred.

In a further embodiment, the inventive agents can comprise non-ionic polymers.

Suitable non-ionic polymers are, for example:

vinyl pyrrolidone-vinyl ester copolymers, such as, for example, those marketed by BASF under the trade name Luviskol®, Luviskol® VA 64 and Luviskol® VA 73, each vinyl pyrrolidone-vinyl acetate copolymers, are likewise preferred non-ionic polymers.

cellulose ethers, such as hydroxypropyl cellulose, hydroxyethyl cellulose, and methyl hydroxypropyl cellulose, as marketed for example under the trademarks Culminal® and Benecel® (AQUALON) and Natrosol® types (Hercules).

starch and its derivatives, especially starch ethers, for example Structure® XL (National Starch), a multifunctional, salt tolerant starch;

shellac polyvinyl pyrrolidones, as are marketed, for example, under the designation Luviskol® (BASF).

The compositions according to the invention preferably comprise the non-ionic polymers in quantities of 0.05 to 10 wt %, based on the total composition. Quantities of 0.1 to 5 wt % are particularly preferred.

Exemplary additional active substances, adjuvants and additives, which can be comprised in the cosmetic agents, are:
structurants such as maleic acid and lactic acid,
swelling agents such as urea, allantoin, carbonates or hydantoin,
dimethyl isosorbitol and cyclodextrins,
dyestuffs to color the agent,
anti-dandruff active materials such as Piroctone Olamine, zinc Omadine and Climbazole,
chelating agents such as EDTA, NTA, β-alanine diacetic acid and phosphonic acids,
opacifiers such as latex, styrene/PVP copolymers and styrene/acrylamide copolymers
pearlizing compositions such as ethylene glycol mono- and distearate as well as PEG-3 distearate,
pigments,
stabilizers for hydrogen peroxide and other oxidizing agents,
propellants such as propane-butane mixtures, $N_2O$, dimethyl ether, $CO_2$ and air,
antioxidants,
perfume oils, scents and fragrances.

With regard to further optional components and their amounts used of these components, reference is expressly made to the relevant handbooks known to the person skilled in the art.

A second subject matter of the invention is a method for treating hair, in which a hair treatment agent according to claim 1 is applied onto the hair and rinsed out of the hair after a contact time.

The contact time is preferably a few seconds to 100 minutes, particularly preferably 1 to 50 minutes and quite particularly preferably 1 to 30 minutes.

A method, in which a cosmetic agent according to claim 1 is applied onto the hair and remains there, is also inventive. "To remain on the hair" is inventively understood to mean that the agent, after its application, is not immediately rinsed out of the hair again. In fact in this case the agent remains for more than 100 minutes on the hair until the next hair wash.

The following examples are intended to illustrate the subject matter of the invention in more detail, without limiting it in any way.

EXAMPLES

All indications of quantities are parts by weight unless otherwise stated. The following formulations were prepared using known production methods Hair Rinse:

| | S1 | S2 | S3 | S4 | S5 | S6 |
|---|---|---|---|---|---|---|
| Stenol ® 1618 | 3.0 | 3.0 | 3.0 | 3.0 | 3.0 | 3.0 |
| Genamin ® KDMP | 2.0 | — | 2.0 | — | — | — |
| Cetrimonium chloride | — | — | — | — | 1.0 | — |
| Rheocare ® Ultragel | 2.0 | — | — | — | — | — |
| Dehyquart ® L80 | 0.5 | — | — | 0.5 | — | — |
| polyquaternium-77 | 0.5 | — | — | 0.5 | — | — |
| Silcare ® SEA | 0.5 | — | 0.5 | — | — | — |
| polyquaternium-71 | 0.5 | — | 0.5 | — | — | — |
| Terraquat ®BD | — | 3.0 | 0.5 | — | 3.0 | 1.0 |
| Dow Corning ® 949 | — | — | — | 0.5 | — | — |
| Stearyldimoniumhydroxy-propyl Laurylglucoside | 0.5 | — | 0.5 | 0.5 | — | — |
| Bis-(ethyl(iso-stearylimidazoline) | 1.0 | 1.0 | 1.0 | 1.0 | 1.0 | 1.0 |
| Panthenol | 0.5 | 0.5 | 0.3 | 0.5 | 0.2 | 0.2 |
| Isopropyl myristate | 0.4 | — | — | — | — | — |
| DC ® 200, 60.000 cSt | 0.3 | — | 0.2 | — | — | — |
| Dicaprylyl carbonate | 0.3 | — | 0.3 | 0.3 | — | 0.5 |
| Titanium dioxide | 0.1 | — | — | — | 0.2 | — |
| Citric acid | — | — | — | 0.3 | — | — |
| Vanillic acid | 0.2 | 0.2 | — | 0.2 | — | — |
| Mandelic acid | — | — | 0.3 | 0.2 | 0.3 | — |
| Methylparaben | 0.2 | 0.2 | 0.2 | 0.2 | 0.2 | 0.2 |
| Water, parfume (0.3%), preservative (0.3%) | ad 100 | ad 100 | ad 100 | ad 100 | ad 100 | ad 100 |

The pH of all formulations was adjusted to 2 to 4.

Hair Cure:

| | K1 | K2 | K3 | K4 | K5 | K6 |
|---|---|---|---|---|---|---|
| Stenol ® 1618 | 6.0 | 6.0 | 6.0 | 6.0 | 6.0 | 6.0 |
| Quartamin ® BTC 131 | 1.5 | — | 0.8 | 1.0 | — | — |
| Crodazosoft ® DBQ | 1.5 | — | — | 1.5 | — | — |
| Rheocare ® Ultragel | 3.0 | — | — | — | — | — |
| Dehyquart ® L80 | 0.5 | — | — | 0.5 | — | — |
| Dehyquart ® F 75 | — | — | — | — | 1.0 | — |
| polyquaternium-77 | 0.5 | — | — | 0.5 | — | — |
| Silcare ® SEA | 0.5 | 0.5 | 0.5 | — | — | — |
| polyquaternium-71 | 0.5 | — | 0.5 | — | — | — |
| Terraquat ® BD | — | 4.5 | 0.5 | 1.5 | 4.5 | 4.5 |
| Dow Corning ® 949 | — | — | — | 0.5 | — | — |
| Stearyldimoniumhydroxy-propyl Laurylglucoside | 0.5 | — | 0.5 | 0.5 | — | — |
| Bis-(ethyl(iso-stearylimidazoline) | 1.0 | 1.5 | 4.0 | 3.0 | 1.5 | 1.0 |
| Benzophenone-4 | 0.5 | — | — | — | 2.0 | — |
| Citric acid | — | — | — | 0.3 | — | — |
| Vanillic acid | 2.0 | 2.0 | — | 0.5 | — | — |
| Mandelic acid | — | — | 0.3 | 2.0 | 0.3 | — |
| Isopropyl myristate | 0.4 | — | 0.4 | — | — | 1.0 |
| Panthenol | 0.5 | 0.5 | 0.8 | 0.5 | 0.5 | 0.5 |
| DC ® 200, 60.000 cSt | 0.3 | — | 0.2 | — | — | — |
| Cetiol ® C5 | 1.0 | — | 0.3 | 0.3 | — | — |
| Dicaprylyl carbonate | 0.3 | — | 0.3 | 0.3 | — | — |
| Methylparaben | 0.2 | — | 0.2 | 0.2 | 0.2 | 0.2 |
| Perfume | 0.3 | 0.3 | 0.3 | 0.3 | 0.3 | 0.3 |
| Phenoxyethanol | 0.4 | 0.4 | 0.4 | 0.4 | 0.4 | 0.4 |
| Water | ad 100 | ad 100 | ad 100 | ad 100 | ad 100 | ad 100 |

The pH of all formulations was adjusted to 2 to 4.

Hair Shampoo:

| | HS1 | HS2 | HS3 | HS4 | HS5 |
|---|---|---|---|---|---|
| Ammonium lauryl ether sulfate (2-EO) | 20.0 | 20.0 | 9.0 | — | — |
| Sodium lauryl ether sulfate (2-EO) | — | — | — | 9.0 | 9.0 |
| Terraquat ® BD | 2.0 | 2.0 | — | — | — |
| Ammonium lauryl sulfate (30% conc.) | 20.0 | 20.0 | — | — | — |
| Cocamidopropyl Betaine | 7.0 | 7.0 | 3.0 | 3.0 | 3.0 |
| Plantacare ® 818 UP | — | — | 6.0 | 6.0 | 6.0 |
| Sodium benzoate | 0.2 | 0.2 | 0.2 | 0.2 | 0.2 |

|  | HS1 | HS2 | HS3 | HS4 | HS5 |
|---|---|---|---|---|---|
| Citric Acid or lactic Acid or a mixture of | 1.0 | 1.0 | 1.0 | 1.0 | 1.0 |
| Thickening agent | 1.0 | 2.0 | 0.5 | 2.5 | 1.0 |
| polyquaternium-77 | 0.5 | — | — | 0.5 | — |
| Silcare ® SEA | 0.5 | — | 0.5 | — | 0.3 |
| Cosmedia ® Guar C261 | — | — | — | 0.4 | — |
| polyquaternium-71 | 0.5 | — | 0.5 | — | 0.1 |
| polyquaternium-74 | — | — | 0.3 | — | 0.2 |
| Dow Corning ® 949 | — | — | — | 0.5 | — |
| Stearyldimonium-hydroxypropyl | 0.5 | — | 0.5 | 0.5 | 0.5 |
| Bis-(ethyl(iso-stearylimidazoline) | 2.0 | 2.0 | 3.0 | 4.0 | 1.0 |
| Benzophenone-4 | — | 0.5 | 0.8 | 0.8 | — |
| Titanium dioxide | 0.2 | — | — | 0.2 | 0.8 |
| Vanillic acid | 2.0 | 2.0 | — | 0.5 | — |
| Mandelic acid | — | — | 0.3 | 2.0 | 0.3 |
| Isopropyl myristate | 0.4 | — | 0.4 | — | — |
| Panthenol | 0.5 | 0.5 | 0.8 | 0.5 | 0.5 |
| DC ® 200, 60.000 cSt | 0.3 | — | 0.2 | — | — |
| Cetiol ® C5 | 1.0 | — | 0.3 | 0.3 | — |
| Dicaprylyl carbonate | 0.3 | — | 0.3 | 0.3 | 0.3 |
| Water, preservative (0.3%), perfume (0.3%) | ad 100 | ad 100 | ad 100 | ad 100 | ad 100 |

The pH of all formulations was adjusted to 4.5 to 5.8.

All thickeners or thickening systems known to the person skilled in the art in surfactant systems can be used as the thickener. For example, cellulose ethers, Xanthan gums, hydroxyethyl celluloses, Laureth-2 and Laureth-3, as well as for example the products under the trade name Antil® or Crothix® are particularly advantageously employed, each individually or in mixtures, in the abovementioned formulations.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A hair treatment agent, comprising:
   a) 0.01 to 15 wt % of a fatty acid amide, relative to the total composition, according to the Formula (I)

Formula (I)

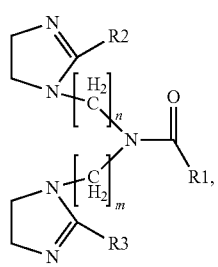

in which R1, R2 and R3 independently of each other stand for a linear branched or unbranched C6 to C30, alkyl or alkylene group, wherein furthermore R2 is the same as R3, and n and m stand independently of one another for whole numbers from 1 to 10, and b) at least one oily body, selected from the group consisting of ester oils, the vegetal oils, and combinations thereof present in an amount of 0.01 to 95 wt % relative to the total composition.

2. The hair treatment agent according to claim 1, further comprising 0.1 to 15.0 wt % of at least one quaternary ammonium compound selected from the group consisting of:

of the cationic surfactants of the Formula (Tkat1)

(Tkat1)

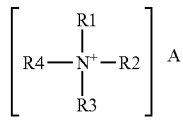

in which R1, R2, R3 and R4 each stand independently of each other for hydrogen, a methyl group, a phenyl group, a benzyl group, for a saturated, branched or unbranched alkyl residue with a chain length of 8 to 30 carbon atoms which can be optionally substituted with one or more hydroxy groups, and A stands for a physiologically acceptable anion;

esterquats;

a compound of the general Formula (I),

Formula (I)

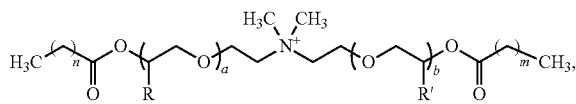

in which n and m independently of one another stand for whole numbers between 5 and 40, with the proviso that n+m≥38;

a and b independently of one another stand for whole numbers between 1 and 10;

R and R' independently of one another are selected from —H and —CH$_3$;

X— is a physiologically acceptable anion;

at least one compound of Formula (II), (II)

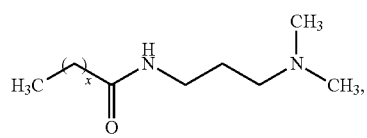

in which x stands for 18, 19, 20, 21, 22, 23 or 24;
a quaternary imidazoline of the Formula (III),

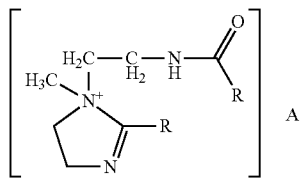

in which the R residues independently of each other each stand for a saturated or unsaturated, linear or branched hydrocarbon residue with a chain length of 8 to 30 carbon atoms and A stands for a physiologically acceptable anion;
poly(methacryloyloxyethyltrimethylammonium compounds);
polyquaternium-24;
polyquaternium-67;
polyquaternium-72;
cationized honey;
polymeric dimethyldiallylammonium salts and their copolymers with esters and amides of acrylic acid and methacrylic acid;
copolymers of vinyl pyrrolidone with quaternized derivatives of dialkylaminoalkyl acrylate and dialkylaminoalkyl methacrylate;
vinyl pyrrolidone-vinylimidazolium methochloride copolymers;
quaternized polyvinyl alcohol;
polyquaternium 2;
polyquaternium-7;
polyquaternium-16;
polyquaternium 17;
polyquaternium 18;
polyquaternium 27;
polyquaternium-69;
polyquaternium-74;
a polymeric alkyl oligoglucoside of the formula

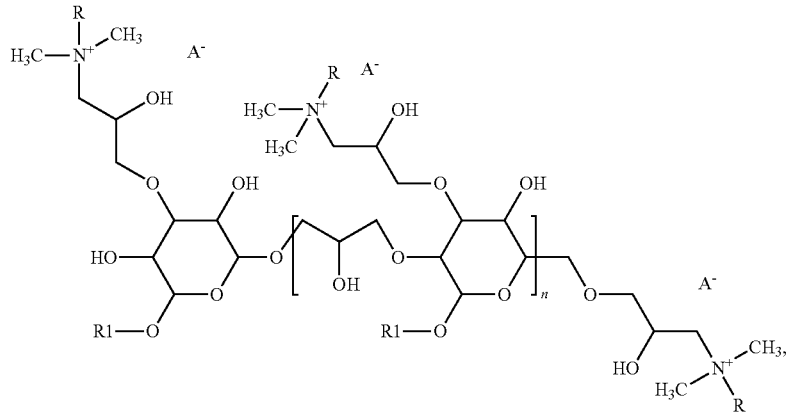

in which R stands for a linear or branched C6 to C30 alkyl residue, a linear or branched C6 to C30 alkenyl residue,
R2 stands for a linear or branched C6 to C30 alkyl residue, a linear or branched C6 to C30 alkenyl residue and
$A^-$ stands for a physiologically acceptable anion;
an oligomeric alkyl oligoglucoside of the formula

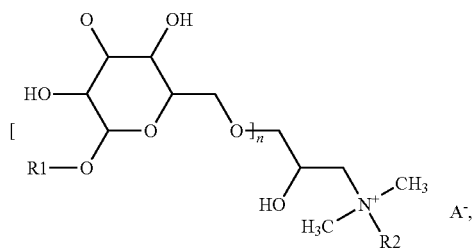

in which R1 stands for a linear or branched C6 to C30 alkyl residue, a linear or branched C6 to C30 alkenyl residue,
R2 stands for a linear or branched C6 to C30 alkyl residue, a linear or branched C6 to C30 alkenyl residue and
$A^-$ stands for a physiologically acceptable anion;
polyquaternium-71, and combinations thereof.

3. The hair treatment agent according to claim 1, further comprising at least one hydroxycarboxylic acid.

4. The hair treatment agent according to claim 1, wherein the oily body includes an ester oils.

5. The hair treatment agent according to claim 1, further comprising a compound selected from the group consisting of carnitine, carnitine tartrate, carnitine magnesium citrate, acetylcarnitine, betalaine, 1,1-dimethylproline, choline, choline chloride, choline bitartrate, choline dihydrogen citrate, N,N,N-trimethylglycine, and combinations thereof 6. The hair treatment agent according to claim 5, wherein the compound is carnitine.

7. The hair treatment agent according to claim 1, further comprising a purine.

8. The hair treatment agent according to claim 7, wherein the purine is caffeine.

9. The hair treatment agent according to claim 1, further comprising ectoin.

10. The hair treatment agent according to claim 1, further comprising at least one ubiquinone.

11. The hair treatment agent according to claim 9, wherein the ubiquinone is co-enzyme Q-10.

12. A method for the treatment of keratinic fibers, comprising:
applying a hair treatment agent to a keratinic fiber, the hair treatment agent comprising,
a) 0.01 to 15 wt % of a fatty acid amide according to the Formula (I)

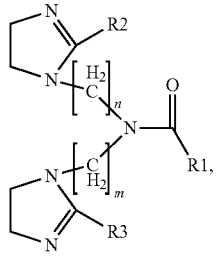

Formula (I)

in which R1, R2 and R3 independently of each other stand for a linear branched or unbranched C6 to C30 alkyl or alkylene group, and n and m stand independently of one another for whole numbers from 1 to 10, and
b) at least one oily body, selected from the group consisting of ester oils, the vegetal oils, and combinations thereof present in an amount of 0.01 to 95 wt % relative to the total composition;
maintaining the hair treatment agent in contact with the keratinic fiber for a contact time of a few seconds to 45 seconds;
rinsing the hair treatment agent from the keratinic fiber.

13. The hair treatment agent according to claim 1, wherein in which R1, R2 and R3 are, independent of each other, a linear branched or unbranched C8 to C24 alkyl or alkylene group.

14. The hair treatment agent according to claim 1, wherein R2 is the same as R3.

15. The hair treatment agent according to claim 1, wherein R1 equals R2 equals R3.

16. The hair treatment agent according to claim 1, wherein n and m stand independently of one another for whole numbers from 2 to 6.

17. The hair treatment agent according to claim 1, wherein n and m stand independently of one another for whole numbers 2, 3, and/or 4.

18. The hair treatment agent according to claim 1, wherein n=m.

19. The hair treatment agent according to claim 2, wherein the at least one quaternary ammonium compound includes a compound of the general Formula (I),

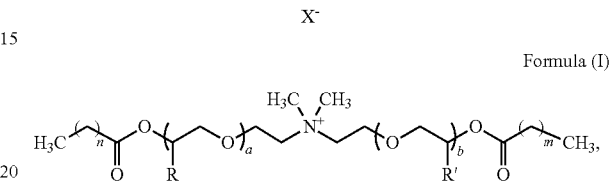

Formula (I)

in which n =m.

20. The hair treatment agent according to claim 2, wherein the at least one quaternary ammonium compound includes a compound of the general Formula (I),

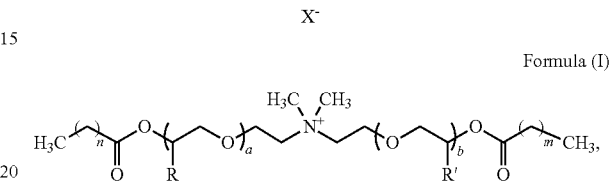

Formula (I)

in which a and b independently of one another stand for whole numbers between 1 and 10 and at least one of the equations a+2≥b≥a−2 or a=b=3 applies.

* * * * *